United States Patent
Lei et al.

(10) Patent No.: US 12,029,398 B2
(45) Date of Patent: Jul. 9, 2024

(54) APPARATUS FOR DETECTING ANALYTE IN A LIQUID SAMPLE

(71) Applicants: Zhejiang Orient Gene Biotech Co., Ltd, Huzhou (CN); Healgen Scientific Limited, Houston, TX (US)

(72) Inventors: Siyu Lei, Huzhou (CN); Jianqiu Fang, Huzhou (CN); Lili Shen, Huzhou (CN)

(73) Assignees: Zhejiang Orient Gene Biotech Co., Ltd, Huzhou (CN); Healgen Scientific Limited, Houston, TX (US)

( * ) Notice: Subject to any disclaimer, the term of this patent is extended or adjusted under 35 U.S.C. 154(b) by 24 days.

(21) Appl. No.: 17/575,196

(22) Filed: Jan. 13, 2022

(65) Prior Publication Data

US 2022/0167952 A1  Jun. 2, 2022

Related U.S. Application Data

(63) Continuation of application No. 16/540,253, filed on Aug. 14, 2019, now Pat. No. 11,234,682.

(30) Foreign Application Priority Data

Sep. 28, 2018  (CN) .......................... 201811139751.6
May 14, 2019  (CN) ......................... 201920681884.X
(Continued)

(51) Int. Cl.
*A61B 10/00* (2006.01)
*A61B 5/15* (2006.01)
*B01L 3/00* (2006.01)

(52) U.S. Cl.
CPC ...... *A61B 10/0051* (2013.01); *A61B 10/0096* (2013.01); *B01L 3/502* (2013.01);
(Continued)

(58) Field of Classification Search
CPC ............ A61B 10/0051; A61B 10/0096; A61B 5/150022; A61B 5/150251;
(Continued)

(56) References Cited

U.S. PATENT DOCUMENTS

2015/0173724 A1* 6/2015 Engel ................. A61B 10/0051
                                                    422/419
2016/0252503 A1* 9/2016 Jian-Feng ............... B01L 3/523
                                                    435/7.1

FOREIGN PATENT DOCUMENTS

JP  2010035972 A  *  2/2010  ......... A61B 10/0045
WO  2010003310 A1    1/2010

* cited by examiner

*Primary Examiner* — Jennifer Wecker
*Assistant Examiner* — Jonathan Bortoli
(74) *Attorney, Agent, or Firm* — NZ CARR LAW OFFICE

(57) ABSTRACT

The present invention discloses an apparatus for detecting analyte in a liquid sample, comprising a cup body; a first receiving area for receiving a liquid sample; a flow-guiding channel through which a sample can be added or collected; the flow-guiding channel is in communication with the first receiving area, the bottom surface of the flow-guiding channel is a slope; wherein, the first receiving area and the flow-guiding channel are disposed in the cup body; the apparatus further comprises a secondary sampling port; the flow-guiding channel is a groove, in which is provided with a second receiving area; and the second receiving area includes a corner area for collecting samples for secondary sampling. The present invention further provides a method of using the apparatus for detecting an analyte in a liquid sample. The apparatus of the present invention can be used for detecting the presence or amount of an analyte in a liquid sample. When a liquid sample has extremely poor fluidity and/or the sample size is very small, the apparatus is still (Continued)

capable of detecting liquid samples, to facilitate operators to draw liquid samples for second confirmatory detection.

10 Claims, 11 Drawing Sheets

(30) Foreign Application Priority Data

May 14, 2019 (CN) .......................... 201920681895.8
May 14, 2019 (CN) .......................... 201920681918.5

(52) U.S. Cl.
CPC . *A61B 5/150358* (2013.01); *B01L 2300/0867* (2013.01); *B01L 2400/0406* (2013.01); *B01L 2400/0481* (2013.01)

(58) Field of Classification Search
CPC ........ A61B 5/150343; A61B 5/150358; B01L 2300/06; B01L 2300/0867; B01L 2300/126; B01L 2400/0406; B01L 2400/0481; B01L 3/502; B01L 3/5023; B01L 3/5029
See application file for complete search history.

APPARATUS FOR DETECTING ANALYTE IN A LIQUID SAMPLE

CROSS REFERENCE TO RELATED APPLICATIONS

The present application is a continuation of co-pending U.S. patent application Ser. No. 16/540,253, filed on Aug. 14, 2019, which claims the benefit of Chinese Patent Application No. 201811139751.6, filed on Sep. 28, 2018, Chinese Patent Application No. 201920681884.X, filed on May 14, 2019, Chinese Patent Application No. 201920681895.8, filed on May 14, 2019, and Chinese Patent Application No. 201920681918.5, filed on May 14, 2019. The content of each aforementioned application including all tables, diagrams and claims is incorporated hereby as reference in its entirety.

FIELD OF THE INVENTION

The present invention relates to an apparatus for detecting analyte in a liquid sample.

BACKGROUND

Currently, there are various kinds of sample collection and testing apparatuses for clinical or home uses available on the markets. Some apparatuses for detecting analytes in samples are described in literatures. U.S. Pat. No. 5,376,337 discloses a saliva sampling apparatus in which a filter paper is used to collect saliva from a subject's mouth and deliver saliva to an indicating reagent. U.S. Pat. Nos. 5,576,009 and 5,352,410 disclose syringe-type fluid sampling apparatus respectively. For these apparatuses, after the initial results are obtained, the collected fluid samples cannot be stored for subsequent confirmatory testing. Chinese patent CN1828307 B discloses an apparatus for detecting an analyte in a fluid sample, which facilitates the sampling for confirmatory testing, however, when the fluid sample has poor fluidity and/or the sample size is small, this apparatus can be used for initial detection only and cannot be used for second confirmatory detection, and in case of extremely poor fluidity of the fluid samples and/or minimal sample size, this apparatus cannot be used for direct detection.

For many other sample collecting and testing apparatuses, it is difficult to use them for sampling and second detection. Many apparatuses have very complicated designs and manufacturing process and require expensive materials.

In addition, in some detecting apparatuses, the test strip, as a detecting element, is generally disposed on a carrier. The carrier may be a plate type or other shaped detection plate, etc. The carrier is generally composed of slots or channels. One slot or one channel can accommodate one test strip, such that the carrier with the test strip can be used alone or in combination with a container. When a carrier with a test strip is inserted into a sample, or a liquid sample is allowed to flow into a container with a carrier, and the amount of liquid sample is large, a large amount of samples will be poured into a slot or a channel, causing "flooding" phenomenon and affecting the normal use of the test strip.

SUMMARY

In order to overcome the drawbacks of the prior art, the technical problem to be solved in the present invention is to provide an apparatus for detecting analyte in a liquid sample.

In a first aspect, the present invention provides an apparatus for detecting analyte in a liquid sample, which can be used for detecting the presence or amount of an analyte in a liquid sample. When a liquid sample has extremely poor fluidity and/or the sample size is very small, this apparatus is still capable of detecting liquid samples. It can facilitate operators to take liquid samples for second confirmatory detection, so as to avoid a large-scale retention of liquid samples at the bottom of the cup body, which may be not conducive to collection or even unable to collect, and thus unable to carry out second confirmatory detection.

In order to solve the foregoing technical problems, the present invention provides the following technical solutions:

An apparatus for detecting analyte in a liquid sample, comprising a cup body; a first receiving area for receiving a liquid sample;

A flow-guiding channel through which a sample can be added or collected; wherein the first receiving area and the flow-guiding channel are disposed in the cup body;

The flow-guiding channel is in communication with the first receiving area, the bottom surface of the flow-guiding channel is a slope, and the first receiving area is at the lowest end of the slope, such that the liquid sample can quickly enter the first receiving area along the flow-guiding channel, and can be gathered in the first receiving area to achieve the detection of samples; when a second confirmatory detection is necessary, the remaining samples of the first receiving area need to be collected and the apparatus can be tilted such that the liquid samples in the first receiving area can smoothly enter the flow-guiding channel and flow along the flow-guiding channel for facilitating the collection of liquid samples.

Further, the flow-guiding channel is a groove, and the groove comprises a bottom surface and a sidewall, wherein the bottom surface of the groove is a slope, and the sidewall of the groove can block the liquid samples from flowing freely in other direction such that the liquid samples flow along the groove to achieve flow guiding, without wasting valuable samples for those with poor fluidity and/or small sample size.

Further, a second receiving area is provided in the groove, and the second receiving area comprises a corner area for collecting samples for secondary sampling, and the corner area is close to the highest end of the slope; when second confirmatory detection is required and the remaining samples in the first receiving area need to be collected, the apparatus can be tilted such that the liquid samples in the first receiving area can flow along the flow-guiding channel and can be collected into the corner area, which facilitates to draw the liquid samples by a pipette or other collection devices in the corner area.

Further, the apparatus further comprises a secondary sampling port which is in communication with the flow-guiding channel. The secondary sampling port is located above the highest end of the groove slope, and diluent or other substance can be added from the secondary sampling port, or samples can be drawn by inserting a straw or a pipette or gun from the secondary sampling port.

Further, one end of the groove is connected to the first receiving area, and the other end of the groove is connected to a side of the cup body, and the secondary sampling port is disposed on the side.

Further, the corner area is close to the secondary sampling port. The corner area is disposed close to the secondary sampling port, and when sampling is necessary, the cup body structure is slightly tilted to allow samples to flow from the first receiving area to the corner area through the groove. At this time, it is convenient to insert a straw from the secondary sampling port to the corner area to draw samples. As the corner area has a function of collection, when the sample size is small, enough samples can be collected for secondary sampling.

Further, the corner area deviates from the central axis position of the secondary sampling port. The corner area deviates from rather than faces the secondary sampling port, so that the straw can be inserted obliquely into the corner area for sampling through the secondary sampling port.

Further, the inlet of the groove is connected to the first receiving area, and the outlet of the groove is connected to the secondary sampling port, the secondary sampling port is located at the upper part of the outlet of the groove. Further, the outlet of the groove is overlapped with the secondary sampling port. The secondary sampling port cooperates with the corner area to facilitate the insertion of the sucking device to the secondary sampling port to take liquid samples from the corner area for second detection or other purposes, or a solvent or other desired substance may be added from the secondary sampling port. For example, adding a solvent increases the size of liquid samples, diluting liquid samples or adding a solvent that lowers the viscosity of liquid samples.

Further, the cross section of the cup body is in a pentagonal shape.

Further, a detecting element is provided in the first receiving area.

Further, the apparatus further comprises a sample collector, the sample collector can be received and held in the cup body, and the sample collector can send the collected samples to the first receiving area through the flow-guiding channel.

Further, the sample collector comprises a collecting element and a push rod.

Further, the cup body is provided with a sleeve for use with the collecting element, the sleeve has a pentagonal inner cover at one end, and the inner cover is fixedly connected with the cup body, the inner cover is provided with an opening, the sleeve has a closed surface at the other end, and a nozzle is provided at the eccentric position of the closed surface.

Further, the cup body may comprise at least one detecting element.

Further, a placement portion for placing a detecting element is further provided on the inner wall of the side of the cup body.

Further, the collecting element is compressible.

Further, the collecting element is a sponge.

Further, a connector for securing the collecting element is provided at one end of the push rod and the other end of the push rod is connected to the fixing base.

Further, the connector is provided with a sealing structure.

Further, the fixing base can cover the sleeve, and the covering surface of the fixing base is provided with a positioning convex portion or a positioning concave portion; the upper surface of the inner cover is provided with a positioning concave portion that cooperates with a positioning convex portion on the fixing base covering surface or the upper surface of the inner cover is provided with a positioning convex portion that cooperates with a positioning concave portion on the fixing base covering surface.

Further, the fixing base has a cylindrical protrusion, and the periphery of the cylindrical protrusion is provided with an external thread; the opening of the inner cover is provided with an internal thread cooperating with the external thread of the periphery of the cylindrical protrusion; the cross section of the fixing base is in a pentagonal shape.

Further, the outer side of the cup body is provided with an anti-slip structure; and the anti-slip structure is a rib or a pit.

The present invention provides an apparatus for detecting the presence or amount of an analyte in a liquid sample, which may comprise a sample collector and a sample receiving cup, the sample collector is used to directly or indirectly collect samples from a patient's body or a site to be collected or in a scene that is separated from a patient's body. The sample receiving cup can receive and hold the sample collector, and in some preferred embodiments, the sample receiving cup can receive the sample collector itself or a part thereof. After collecting samples, the sample collector can be put into the sample receiving cup, and then the sample is transferred to the sample receiving cup; in some preferred embodiments, the sample receiving cup can directly receive the samples collected by the sample collector.

In some preferred embodiments, the sample receiving cup comprises at least one detecting element for detecting the presence or amount of an analyte in a sample.

In some preferred embodiments, the detection apparatus may have a plane that enables the whole apparatus to be in a stationary state when it is placed horizontally. The term "stationary state" means that it does not roll arbitrarily. Since the detecting element may be flat, it needs to be laid flatly for testing. At this time, ensure that it does not roll after placement, affecting the detection. In some preferred embodiments, the detection apparatus may have at least one of the above planes. In some preferred embodiments, the outer wall of the detection apparatus may be composed of at least three of the above planes.

In some preferred embodiments, the sample collector comprises a collecting element for collecting a liquid sample, and a push rod for fixing the collecting element.

In some preferred embodiments, the sample receiving cup comprises a cup body, and the cup body is fixedly connected with a sleeve for cooperating with the collecting element, and the sleeve is capable of receiving and holding the sample collector.

In some preferred embodiments, the collecting element is compressible, by which it compresses or rebounds to squeeze or draw samples. In some preferred embodiments, the collecting element is fixedly mounted on the sample collector by a connector, and in some preferred embodiments, the collecting element is detachably connected to the sample collector. In some preferred embodiments, the sample collector is provided with a component for connecting the collecting element, and the component may be a connecting rod, such that the collecting element can be inserted into the sample collector to place samples after samples are collected.

In some preferred embodiments, the collecting element is a sponge which may be natural or synthetic. In some preferred embodiments, the collecting element is a cylindrical sponge material suitable for being placed in a subject's mouth to collect saliva. In a special embodiment, the collecting element is treated with a chemical component (for example, a citrate or other chemicals) to promote salivation and facilitate absorption by the collecting element.

In some preferred embodiments, the collecting element is fixed on a connector at one end of the push rod. In some preferred embodiments, the collecting element can be attached or welded to the collector of the push rod by a sealant or a hot melt adhesive or other adhesives. In some preferred embodiments, the connector has a sealing structure, for example, a sealing ring. The sealing structure on the connector can fit the inner wall of the sleeve and ensure that the samples collected will not flow back when the connector is pressed down.

In some preferred embodiments, the push rod is connected to the fixing base at one end away from the connector. The cross-sectional area of the fixing base is larger than the cross-sectional area of the push rod, so the fixing base is disposed to facilitate operators to grab the sample collector. In some preferred embodiments, the push rod and the fixing base may be fixedly connected by integral molding, and in some preferred embodiments, may be connected by other suitable means, for example, by snapping, or by bonding or cooperation of internal and external threads. In some preferred embodiments, the fixing base covering surface has a cylindrical protrusion. The fixing base covering surface refers to a contact surface in contact with the upper surface of the sleeve when the fixing base covers the sleeve. The push rod is fixedly connected to the cylindrical protrusion by integral molding. In some preferred embodiments, the periphery of the cylindrical protrusion is provided with an external thread. In some preferred embodiments, the fixing base is provided with an internal thread for detachably connecting the sleeve. In some preferred embodiments, the fixing base is provided with other suitable structures for detachably connecting the sleeve, for example, a buckle structure or other parts that fit snugly and hold the two members together.

In some preferred embodiments, the fixing base can completely cover the sleeve, and the term "completely cover" herein means that, when fixing base completely covers the sleeve, a sealing structure is formed, and liquid samples cannot leak through the cover from the apparatus. In the process of completely covering the sleeve by the fixing base, the collecting element is constantly compressed.

In some preferred embodiments, a positioning convex portion or a positioning concave portion is disposed on the covering surface of the fixing base. The positioning convex portion or the positioning concave portion is disposed on the covering surface, without affecting the external structure of the fixing base or the cup body, and the structure outside the apparatus will not affect the positioning of the apparatus. In some preferred embodiments, the positioning convex portion may be a positioning block, and the positioning concave portion may be a positioning groove. In some preferred embodiments, an arc-shaped positioning block is provided on the fixing base covering surface, and the arc-shaped positioning block is connected to the end of the external thread of the cylindrical protrusion, such that the arc-shaped positioning block is smoothly screwed into a corresponding positioning groove for positioning after the external thread is screwed completely.

In some preferred embodiments, a reinforcing structure is provided on the inner wall of the fixing base for reinforcing the sidewall of the fixing base, so that the fixing base is more firm and stable and is not easily damaged. In some preferred embodiments, the reinforcing structure is a blade-shaped structure which has good reinforcing effect. The fixing base is firm and is not easily damaged, with an attractive appearance. In other embodiments, the reinforcing structure can be a plate or any other suitable structure.

In some preferred embodiments, the sleeve has a connecting part at one end, which can connect the cup body and facilitate to use the sleeve with the sample collector. In some preferred embodiments, the sleeve has an inner cover at one end, the inner cover can cover the cup body opening, and the inner cover is provided with opening to facilitate the insertion of the collecting element into the sleeve. In some preferred embodiments, the sleeve has a closed surface at the other end, and the closed surface closes the other end of the sleeve. In some preferred embodiments, a nozzle is provided at the eccentric position of the closed surface, to facilitate the flow of the liquid sample from the nozzle after being compressed. In some preferred embodiments, the sleeve is tapered, the inner cover opening has an inner diameter larger than the diameter of the closed surface, and the diameter of the closed surface is larger than the outer diameter of the nozzle. The inner cover opening has an inner diameter larger than the maximum cross-sectional width of the collecting element, and the diameter of the closed surface is smaller than the minimum cross-sectional width of the collecting element. After collecting the liquid sample, the collecting element is inserted from the inner cover opening into the sleeve, and in the process of continuous insertion into the sleeve, the collecting element is not only subjected to the thrust of the push rod, but also the squeezing of the inner wall of sleeve on the periphery, so that the liquid sample can be quickly and completely removed from the collecting element. In other embodiments, the sleeve may also be in other shape that matches with the shape of the collecting element.

In some preferred embodiments, the inner cover of the sleeve is fixedly connected to the cup body and may be attached or welded to the opening end of the cup body. In other embodiments, they can be fixed by other suitable means. In some preferred embodiments, an internal thread that matches with the external thread of protruded periphery of the fixing base at the opening of the sleeve inner cover. The upper surface of the sleeve inner cover is provided with an arc-shaped positioning groove that cooperates with the arc-shaped positioning block on the covering surface of the fixing base. By rotating the fixing base, the external thread on the fixing base is continuously screwed into the internal thread at the inner cover opening until the inner cover is completely covered and the arc-shaped positioning block is also completely screwed into the arc-shaped positioning groove. The arc-shaped positioning block cooperates with the arc-shaped positioning groove to limit the movement of the fixing base in the tightening direction, but allow the fixing base to move in the opposite direction under the action of the external force to open the fixing base. The setting of the positioning block and the positioning groove makes operators to feel completely covering the inner cover by the fixing base, to avoid tightening the fixing base with a great force after the inner cover is tightened and covered, which may easily damage the fixing base; in addition, as operators are not sure whether to tighten, they may tighten the fixing base for multiple times, which wastes the time and affects the operation efficiency. After the rotation is completed, the fixing base completely covers the sleeve opening to form a sealing structure. The liquid sample cannot leak from the apparatus through the cover, and the positioning block is screwed into the positioning groove to give a rotation indication, so that operators can clearly know that the apparatus has been completely covered and there is no need to tighten the fixing base. During the rotation, by squeezing the collecting element that has absorbed liquid samples, the liquid samples on the collecting element are squeezed from the nozzle into the sample receiving cup.

In some preferred embodiments, the fixing base and/or the cup body may be in the shape of a polyhedron. In some preferred embodiments, the fixing base and the cup body are both polyhedral shapes, that is, the fixing base and the cup body may have polygonal cross sections, which may be triangles, quadrangle, pentagons or other polygons, or may be regular polygons or non-regular polygons. In some preferred embodiments, one or more detecting elements may be disposed in the cup body of the polyhedron shape to detect different analytes in the sample simultaneously. In some preferred embodiments, the detecting element may be disposed on any of the side inner wall of the polyhedron cup body, and any of the side inner walls of the cup body may be provided with a placement portion for placing the detecting element. In some preferred embodiments, the cup body is an irregular pentahedron, that is, the cup body has an irregular pentagon shape in cross section, wherein the inner wall of the side surface of the pentahedron cup body with the maximum area is provided with a detecting element placement portion for placing detecting element. In some preferred embodiments, the inner cover has the same shape and side length as those of the cross section of the cup body, and it is also an irregular pentagon shape. Therefore, the inner cover can tightly cover the opening of the cup body, and each side of the inner cover does not extend beyond the side of the cup body, so that the cup body can be placed horizontally and stably on the side.

In some preferred embodiments, the fixing base and the cup body may be polyhedrons having the same number of faces, or polyhedrons having different numbers of faces. In some preferred embodiments, both the fixing base and the cup body are irregular pentahedrons. After the fixing base completely covers the cup body, the fixing base with the largest area is aligned with one side of the cup body with the largest area, so that it is convenient for confirming that the fixing base has completely covered the cup body. In some preferred embodiments, the fixing base is close to the side length of the pentagon of the cup body cross-section. When the fixing base completely covers the cup body, each side of the fixing base is nearly flush with each side of the cup body, almost at the same plane, so that the fully covered apparatus can be placed flatly on the side to facilitate scanning of the test results.

In some preferred embodiments, the cup body is made of a transparent material, to facilitate the observation of test results.

In some preferred embodiments, a secondary sampling port is provided on one side of the cup body. In some preferred embodiments, a lower part of one side of the cup body is provided with an arch-shaped recessed portion, and a secondary sampling port is disposed at the arch-shaped recessed portion. The plug can block the secondary sampling port. After the plug blocks the secondary sampling port, the side with the secondary sampling port can still be placed flatly on the side. In some embodiments, the secondary sampling port may be capped with a plug during the sample testing and the apparatus transport for sealing. When the apparatus is received on the clinical test equipment, the plug can be removed and users can take out samples from the secondary sampling port for second confirmatory detection. The setting of the secondary sampling port allows users to add solvent or other required substances from the secondary sampling port, for example, adding solvent. The addition of solvent increases the amount of liquid sample, and the sample solution is diluted or the solvent that can lower the viscosity of a liquid sample can be added. In some embodiments, operators can conveniently take the samples using a straw or other sampling device when the plug is opened. The sample receiving cup can be conveniently held in a closed state, and liquid sample is still allowed to be taken out.

In some preferred embodiments, an anti-slip structure is provided on the outer side of the cup body. In some preferred embodiments, and the anti-slip structure is a rib, the setting of the rib makes users to easily hold or grasp the sample receiving cup, and avoid slipping and falling to damage the sample receiving cup. In some preferred embodiments, the outer side of the cup body is provided with other anti-slip structures, for example, a pit or any other suitable structure.

In some preferred embodiments, a sample receiving cup is provided with a first receiving area for receiving and storing a sample; and in some preferred embodiments, the sample receiving cup is further provided with a flow-guiding channel through which a sample can be added or collected; the first receiving area is in communication with the flow-guiding channel, so that the samples can move between them. In some preferred embodiments, the first receiving area and the flow-guiding channel are both disposed at the bottom of the cup body.

In some preferred embodiments, the sample receiving cup may comprise at least one detecting element for detecting the presence or amount of analyte in a sample. In some preferred embodiments, the detecting element may be distributed on the inner wall of one side of the apparatus herein, or the inner walls of a plurality of sides of the apparatus herein. In some preferred embodiments, the inner wall of the side of the cup body is further provided with a placement portion for placing a detecting element, and the detecting element may be placed in the placement portion. The placement portion is connected to the side inner wall of the cup body. In some preferred embodiments, the placement portion is detachably connected to the inner wall of the side of the cup body.

In some preferred embodiments, the placement portion may be a detection plate. In some preferred embodiments, the placement portion may be provided with a slot, in some preferred embodiments, the detecting element may be a strip or similar strip, and these strips or similar strips may be placed in the slot. In some preferred embodiments, one slot can be disposed on one detection plate, and in some other preferred embodiments, a plurality of slots can be disposed on one detection plate.

In some preferred embodiments, the detecting element may be any test device that provides a test result. In some preferred embodiments, the detecting element is a test strip, and the test strip may have specific binding molecule immobilized thereon and a reagent for immunoassay. In some preferred embodiments, the detecting element may also be a chemical reaction-based test reagent, a biological-based test reagent (e.g., an enzyme assay or ELISA assay), or a fluorescent test reagent, etc. Moreover, in some other embodiments, there are some other reagents on the detecting element, and these reagents can be used to detect the presence or amount of an analyte in the sample. In some embodiments, the detecting element comprises an agent for detecting the presence of drug abuse.

In some preferred embodiments, the sample in which the analyte is detected in the present invention may be any fluid sample. Fluid samples suitable for testing using the present invention include oral fluid, saliva, whole blood, serum, plasma, urine, spinal fluid, biological extracts, mucus, and tissues. "Saliva" refers to the secretions of the salivary glands. "Oral fluid" refers to any fluid present in the oral cavity. The analyte to be detected can be any analyte, and the detecting element can be made for the analyte.

In some preferred embodiments, the first receiving area is disposed at the lower part of the detecting element. The liquid sample in the first receiving area can reach the detecting element, so that the detecting element can detect the sample. In some embodiments, the absorbent material absorbs the liquid sample of the first receiving area and delivers it to the detecting element, providing a fluidic communication between the first receiving area and the detecting element such that the absorbent material will not absorb and transport more liquid samples than the amount that can be loaded on the detecting element, to cause an overflow on the detecting element. A "fluidic communication" structure means that fluid from one structure will encounter another structure that is in fluidic communication therewith. Thus, when the first receiving area is in fluidic communication with the detecting element, the liquid sample of the first receiving area reaches the detecting element through the absorbent material. The first receiving area, the absorbent material, and the detecting element may be in direct physical contact, or there may be gaps between them but remain in fluidic communication. An "absorbent material" is a material that absorbs liquid and can transport liquid by capillary action. Absorbent materials include, but are not limited to, filter paper or other types of absorbent paper, specific nylons, nitrocellulose, and other materials having such characteristics. In some preferred embodiments, there may be no absorbent material, and the fluidic communication between the first receiving area and the detecting element can be maintained, and the liquid samples of the first receiving area can still reach the detecting element.

In some preferred embodiments, the flow-guiding channel is connected to the first receiving area and the other side inner wall of the cup body; in some preferred embodiments, the flow-guiding channel is connected to the first receiving area and the other side inner wall of the cup body, here, the other side is the side where the secondary sampling port is located.

In some preferred embodiments, the flow-guiding channel may be a groove; the groove comprises a bottom surface and a sidewall, and provides a passage for the liquid samples. In some preferred embodiments, a second receiving area is provided in the groove, and the second receiving area is connected to the side inner wall of the cup body. This side is the side where the secondary sampling port is located. The setting of the groove facilitates the flow-guiding and collection of liquid samples, avoiding the liquid samples from flowing to a large area randomly, which is not conducive to collecting the liquid sample for second detection; and avoiding waste of the liquid sample, especially for liquid samples with poor fluidity and/or very small size, the setting of the groove is very important, which avoid a large area of retention of liquid samples with poor fluidity and/or very small size in the bottom of the cup body, causing difficulty or failure to collect, and unable to perform a second detection.

In some preferred embodiments, the nozzle extends into the groove, but does not touch the groove bottom surface, such that liquid samples are in contact with the groove bottom surface after squeezed out of the nozzle. The sidewall of the groove can block part of the liquid sample from splashing from the groove. In some preferred embodiments, the nozzle is closer to the groove inlet, so the nozzle is closer to the first receiving area, so that the flow path of the liquid sample is the shortest, to reach the first receiving area quickly. For liquid samples with poor fluidity and/or very small size, it can effectively avoid the waste and loss.

In some preferred embodiments, the bottom surface of the groove is set to a slope, and the first receiving area is at the lower end of the slope, such that the liquid samples can be smoothly flowed into the first receiving area, to effectively avoid the retention of liquid samples with poor fluidity and/or very small size on the contact surface in contact with the liquid and prevent influence on the detection of liquid samples.

In some preferred embodiments, the groove inlet is connected to the first receiving area, and the groove outlet is connected to one side of the cup body. In some preferred embodiments, the groove outlet is connected to a side opposite to the side of the detecting element, here, the opposite side means the side of the cup body that is not adjacent to the side of the detecting element and is the side where the secondary sampling port is located.

In some preferred embodiments, the groove inlet is lower than the groove outlet. When the liquid sample is ejected from the nozzle, it contacts the groove and flows into the first receiving area along the groove. The lower inlet of the groove can accelerate the smooth flow of the liquid sample into the first receiving area. When the second confirmatory detection is required, the plug can be opened and the cup body can be tilted. The liquid sample of the first receiving area can enter the groove from the groove inlet, and flow to the second receiving area along the groove channel, so that operators can draw the liquid samples.

In some preferred embodiments, the second receiving area may comprise a corner area, which is used to collect samples for secondary sampling. In some preferred embodiments, a sidewall of the groove is provided with a corner, and the corner may be a right angle, a rounded corner, a chamfer, a sector angle and other suitable shapes. When the cup body is tilted, the corner is arranged to facilitate the collection of liquid samples in the corner area, to facilitate to collect and draw liquid samples.

In some preferred embodiments, a corner area is provided near the secondary sampling port. When sampling is required, the cup body structure is slightly tilted, to allow samples to flow from the first receiving area to the corner area through the groove. At this time, it is convenient to insert a straw from the secondary sampling port and easy to reach the corner area to draw samples. As the corner area has the function of collection and even if the sample size is small, enough samples can be collected for secondary sampling.

In some preferred embodiments, the corner area is not directly facing but deviates from the secondary sampling port. The "deviate" means that the corner area is not on the same line as the central axis of the secondary sampling port, but deviates from the central axis, by this way, the straw is inserted obliquely through the secondary sampling port to reach the corner area for sampling.

In some preferred embodiments, the outlet of the groove is connected to the secondary sampling port, the secondary sampling port is located at the upper part of the outlet of the groove. Further, the outlet of the groove is overlapped with the secondary sampling port. In some preferred embodiments, half of the area of the secondary sampling port overlaps with the groove outlet, the secondary sampling port cooperates with the corner area to facilitate the insertion of the sucking device to the secondary sampling port to take liquid samples from the corner area for second detection or other purposes, or a solvent or other desired substance may be added from the secondary sampling port. For example, adding a solvent increases the size of liquid samples, diluting liquid samples or adding a solvent that lowers the viscosity of liquid samples.

The present invention further provides a method of using the apparatus for detecting an analyte in a liquid sample. The collecting element of the sample collector absorbs a certain amount of the liquid sample, then the sample collector is inserted into the sleeve, the fixing base is rotated until the sleeve opening is completely covered, the liquid sample cannot leak from the apparatus through the cover, and the positioning block is screwed into the positioning groove to give a rotation indication. During the rotation, by squeezing the collecting element that has absorbed liquid samples, the liquid samples on the collecting element are squeezed from the nozzle, and liquid samples flow from the bottom surface of the groove to the inlet of the groove, and to the first receiving area, and the liquid sample of the first receiving area reaches the detecting element, which is detected on the detecting element. After a period of time for testing, the presence and amount of the analyte in the liquid sample is determined. When a second confirmatory detection is required, the plug is opened and the sample receiving cup body is tilted. The remaining liquid sample in the first receiving area enters the groove from the groove inlet and flows along the groove and is collected in the corner area. The sampler can be inserted from the secondary sampling port to the liquid sample of the corner area, to draw liquid samples, which are reserved for second confirmatory detection.

In a second aspect, the present invention provides an apparatus for detecting analyte in a liquid sample, which can be used for detecting the presence or amount of an analyte in a liquid sample. When the liquid sample size is big, the apparatus can still be used to detect liquid samples, to facilitate operators to draw liquid samples for second confirmatory detection.

In a preferred embodiment, the apparatus comprises a cup body, and the cup body includes a sidewall and a bottom. A first liquid collecting area is provided at the bottom of the cup body, wherein a second liquid collecting area is further provided at the bottom of the cup body.

Preferably, the cup body bottom further includes a protrusion structure protruding into the cup body, and the part of second liquid collecting area is disposed on the protrusion structure.

Preferably, the second liquid collecting area is a chamber.

Preferably, the second liquid collecting area is in fluidic communication with the first liquid collecting area.

Preferably, the apparatus further comprises a secondary sampling port, and the secondary sampling port is a puncturable structure.

Preferably, the secondary sampling port is disposed on a cup body sidewall opposite to the opening of the second liquid collecting area.

Preferably, the apparatus further comprises a detecting element, and the sampling loading area or part of the sampling loading area of the detecting element is located in the first liquid collecting area.

Preferably, the detecting element is disposed in a placement portion for placing a detecting element.

Preferably, the apparatus further comprises a sample collector, and the sample collector can be received and held in the cup body, and the collected samples are sent to the first liquid collecting area.

Preferably, the sample collector comprises a collecting element and a push rod.

Preferably, the collecting element is made of a sponge or a foam material.

Preferably, the apparatus further comprises a sleeve, the sleeve has an opening at one end and a closed surface at the other end, and a notch for allowing the liquid to flow out is disposed on the closed surface.

Preferably, the notch is located above the protrusion structure.

In another preferred embodiment, the apparatus comprises a cup body, and the cup body includes a sidewall and a bottom. The bottom of the cup body is convex toward the cup body to form a protrusion structure, and a first liquid collecting area is formed between the protrusion structure and the cup body sidewall, wherein the protrusion structure is used to guide liquid samples to enter the first liquid collecting area.

Preferably, the protrusion structure comprises a central top portion, and a slope extending from the central top portion to the first liquid collecting area along the periphery, and the liquid sample enters the first liquid collecting area via the surface of the slope.

Preferably, the slope is composed of a plurality of curved surfaces that are curved inwardly.

Preferably, the plurality of curved surfaces has different radians.

Preferably, the liquid sample enters the first liquid collecting area via one or more curved surfaces of the protrusion structure.

Preferably, the protrusion structure comprises a first curved surface, a second curved surface, and/or a third curved surface, wherein an end of the third curved surface is connected to the first liquid collecting area, and the liquid sample enters the first liquid collecting area through the second curved surface and the third curved surface.

Preferably, the end of the third curved surface corresponds to the sample loading area of the detecting element.

Preferably, there is a smooth boss between the second curved surface and the third curved surface.

Preferably, both sides of the second curved surface and/or the third curved surface have structures restricting liquid flow.

Preferably, the structure for restricting liquid flow is a curved surface having a height higher than the second curved surface and/or the third curved surface.

Preferably, the protrusion structure further comprises a second liquid collecting area.

Preferably, the second liquid collecting area is a chamber.

Preferably, the opening of the second liquid collecting area is located on one of the curved surfaces that constitute the protrusion structure.

Preferably, the opening of the second liquid collecting area is located on the third curved surface.

Preferably, the second liquid collecting area is in fluidic communication with the first liquid collecting area.

Preferably, the apparatus comprises a secondary sampling port, and the secondary sampling port is a puncturable structure.

Preferably, the secondary sampling port is disposed on the cup body sidewall opposite to the opening of the second liquid collecting area.

Preferably, the apparatus further comprises a detecting element, and the sampling loading area or part of the sampling loading area of the detecting element is located in the first liquid collecting area.

Preferably, the detecting element is disposed in a placement portion for placing a detecting element.

Preferably, the apparatus further comprises a sample collector, and the sample collector can be received and held in the cup body, and the collected samples are sent to the first liquid collecting area.

Preferably, the sample collector comprises a collecting element and a push rod.

Preferably, the collecting element is made of a sponge or a foam material.

Preferably, the apparatus further comprises a sleeve, the sleeve has an opening at one end and a closed surface at the other end, and a notch for allowing the liquid to flow out is disposed on the closed surface.

Preferably, the notch is disposed above one of the curved surfaces of the protrusion structure.

Preferably, the notch is disposed above the second curved surface of the protrusion structure.

In a third aspect, the present invention provides a placement portion capable of preventing a flooding of a test strip.

Preferably, the placement portion comprises a slot for accommodating a test strip, wherein the slot includes an anti-flooding structure, and the anti-flooding structure includes a recess disposed on the slot bottom plate.

Preferably, the slot forms a chamber for accommodating excess sample at the recess.

Preferably, there are one or more chambers.

Preferably, the chamber is rectangular.

Preferably, the card slot sidewall having a recess has a protrusion for clamping the test strip.

Preferably, the chamber is located in the sample loading area of the test strip, or upstream of the labeled area of the test strip, or between the sample loading area and the labeled area of the test strip.

Preferably, the anti-flooding structure divides the slot into two parts, i.e. a first portion having a recess on the slot bottom plate and a second portion having no recess on the slot bottom plate, wherein the width of the first portion is greater than that of the second portion.

Preferably, the second portion further includes a third portion having a width greater than the second portion.

Preferably, the third portion has a smaller width than the first portion.

Preferably, the third portion is located between the first portion and the second portion.

Preferably, the third portion is located in the sampling loading area of the test strip, or downstream of the sample loading area of the test strip, or between the sampling loading area and the labeled area of the test strip, or in the labeled area of the test strip.

Preferably, the width of the second portion is equal to or substantially equal to the width of the test strip.

The present invention can achieve the following beneficial effects.

(1) The present invention is provided with a flow-guiding channel at the bottom of the apparatus, and the flow-guiding channel is groove, which is beneficial to collection and detection of samples, and avoids large-scale retention of samples with poor fluidity and/or small sample size at the bottom of the cup body to waste samples, causing failure to collect samples for second detection.

(2) The groove bottom surface of the present invention is a slope, and the groove inlet is lower than the groove outlet, which can accelerate the flow of liquid samples into the first receiving area, improve the collection and detection efficiency, and avoid the retention of samples with poor fluidity and/or a small sample size in the slope and cannot flow into the first receiving area smoothly, affecting the detection.

(3) A sidewall of the groove of the present invention is provided with a corner, and the corner is provided to collect samples into the corner area. When sampling is required, the cup body is slightly tilted, allowing samples to flow from the first receiving area to the corner area through the groove. At this time, it is convenient to insert a straw from the secondary sampling port to the corner area to draw samples. As the corner area has a function of collection, when the sample size is small, enough samples can be collected for secondary sampling.

(4) The secondary sampling port of the present invention is in the upper part of the groove outlet, and the secondary sampling port overlaps with the groove outlet to facilitate the insertion from the secondary sampling port to take out samples for the second confirmatory detection, in addition, a solvent or other desired substance may be added from the secondary sampling port.

(5) The cup body of the present invention is made of a transparent material to facilitate observation of test results.

(6) In the present invention, a positioning convex portion or a positioning concave portion is provided on the covering surface of the fixing base. The sleeve inner cover is provided with a recess that cooperates with the positioning convex portion on the covering surface of the fixing base, or the inner cover is provided with a boss that cooperates with the positioning concave portion on the covering surface of the fixing base. The cooperation of the boss and the recess makes operators to feel completely covering the inner cover by the fixing base, to avoid tightening the fixing base with a great force after the inner cover is tightened and covered, which may easily damage the fixing base; in addition, as operators are not sure whether to tighten, they may tighten the fixing base for multiple times, which wastes the time and affects the operation efficiency. The setting of the positioning convex portion or positioning concave portion on the covering surface rather than other position may not affect the fixing base or the external structure of the cup body; in addition, the external structure of the apparatus may not affect the positioning of the apparatus.

(7) The fixing base and the cup body of the present invention are irregular pentahedrons, and the size of the fixing base is close to the cross-sectional polygon size of the cup body. When the fixing base completely covers the cup body, one side of the fixing base is in flush with one side of the cup body, so that the fully covered apparatus can be placed flatly on the side to facilitate scanning of the test results, avoid the rolling or sliding of the cup body to damage the detection cup and cause leakage and contamination of samples in the cup body.

(8) The anti-slip structure is provided on the outer side of the cup body of the present invention. With the setting of the anti-slip structure, users can easily grasp or hold the sample receiving cup, avoiding slipping and falling to damage the detection apparatus.

(9) A reinforcing structure is provided on the inner wall of the fixing base in the present invention. With the setting of the reinforcing structure, the fixing base is more stable and firm and is not easily damaged. The use of the blade-shaped reinforcing structure achieves better reinforcing effect. The fixing base is overall firm and is not easily damaged, and it looks good.

(10) In the present invention, the nozzle is disposed in the eccentric position of the closed surface. The nozzle extends into the groove but does not contact the groove bottom surface, such that liquid samples are in contact with the groove bottom surface after squeezed out of the nozzle. The sidewall of the groove can block part of the liquid sample from splashing from the groove. In addition, the nozzle is closer to the groove inlet, so the nozzle is closer to the first receiving area, so the flow path of the liquid sample is the shortest, to reach the first receiving area quickly. For liquid samples with poor fluidity and/or very small size, it can effectively avoid the waste and loss.

(11) A second liquid collecting area is provided on the bottom of the apparatus in the present invention. The second liquid collecting area can facilitate collection of samples for second detection; in addition, the second liquid collecting area can store liquid samples in case of excessive samples to prevent flooding of the detecting element.

(12) In the present invention, the protrusion structure at the bottom of the apparatus, as a flow-guiding structure, guides liquid samples from the collecting element into the target area rather than the non-target area. By setting the protrusion structure as a slope constituted by curved surfaces having different curvatures, it can, on the one hand, exerts a flow-guiding effect to guide liquid to enter the target area uniformly such that each detecting element can contact sample at the same time, and on the other hand, exerts a flow-buffering effect, to prevent a large amount of liquid samples from rapidly entering the target area to cause shock on the detecting element, ensuring the stability of the test results.

(13) The placement portion for accommodating testing element is provided with a chamber for accommodating excess liquid at the bottom, and the slot of the placement portion is set to different width, to effectively prevent a flooding phenomenon of the detecting element caused by capillary force of liquid samples in the placement portion, guarantee the effective and smooth detection, and improve the sensitivity and reliability of the detection.

Figure 1:
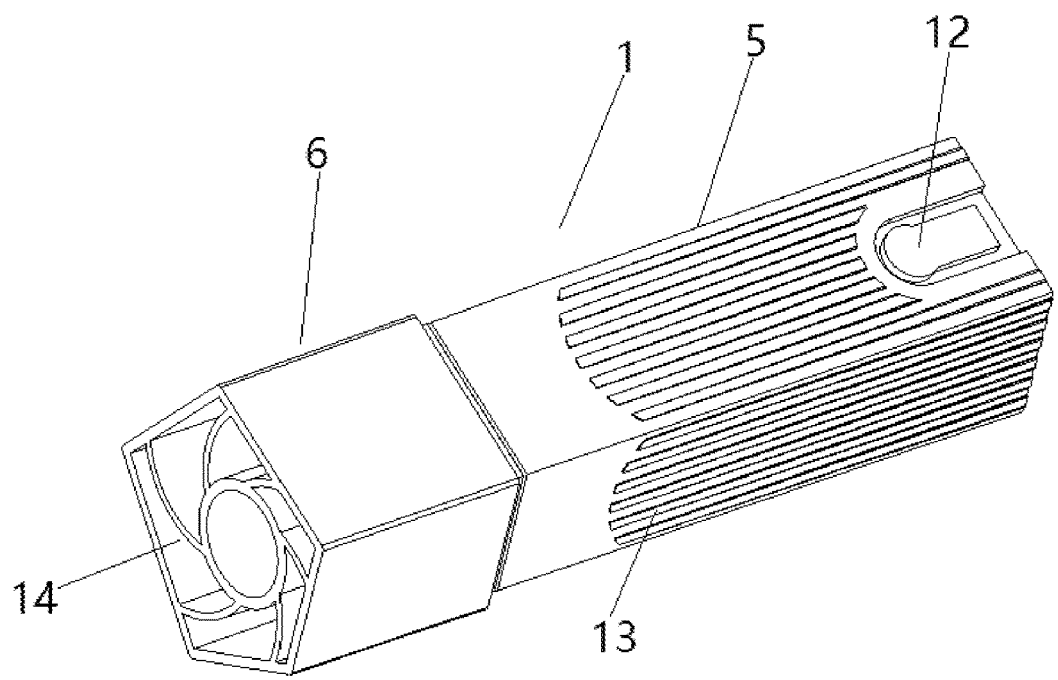
FIG. 1 is a schematic structural view of the apparatus of the present invention.

Notes: sample receiving cup 1, sample collector 2, detecting element 3, back side 301, sample loading area 302, labeled area 303, detecting area 304, water absorption area 305, protrusion structure 4, central top portion 40, first curved surface 41, second curved surface 42, third curved surface 43, fourth curved surface 44, fifth curved surface 45, sixth curved surface 46, smooth boss 47, cup body 5, cup body sidewall 50, first liquid collecting area 51, second liquid collecting area 52, opening 520, straight surface 521, slope 522, fixing base 6, positioning block 7, positioning groove 8, protrusion 9, secondary sampling port 11, plug 12, anti-slip structure 13, reinforcing structure 14, collecting element 15, sleeve 16, notch 161, push rod 17, connector 18, nozzle 19, first receiving area 20, flow-guiding channel 21, placement portion 22, corner 23, groove inlet 24, inner cover 25, covering surface 26, closed surface 27, slot 28, corner area 29, blocking strip 30, bottom surface 31, sidewall 32, head portion 181, middle portion 182, end portion 183, base layer 221, one end of base layer 222, another end of base layer 223, slot opening 280, slot sidewall 281. 282, bottom plate 283, tenon structure 284, first portion 285, second portion 286, third portion 287, recess 288, chamber body 289, first chamber body 2891, second chamber body 2892, protrusion 290, thickness mark 220.

DETAILED DESCRIPTION

The technical solutions of the present invention are further described in detail below with reference to the accompanying drawings. It is to be understood that specific embodiments are illustrative of the present invention and not intended to limit the present invention.

Example 1

As shown in FIG. 1, the present invention provides an apparatus for detecting the presence or amount of an analyte in a liquid sample, the detecting device being in an assembled state. The detection apparatus may comprises a sample collector and a sample receiving cup 1, the sample collector is used to directly or indirectly collect samples from a patient's body or a site to be collected or in a scene that is separated from a patient's body.

The sample receiving cup 1 can receive and hold the sample collector, and in some preferred embodiments, the sample receiving cup 1 can receive the sample collector itself or a part thereof. After collecting samples, the sample collector can be put into the sample receiving cup 1, and then the sample is transferred to the sample receiving cup 1; in some preferred embodiments, the sample receiving cup 1 can directly receive the samples collected by the sample collector.

In some preferred embodiments, the sample receiving cup comprises at least one detecting element for detecting the presence or amount of an analyte in a sample.

In some preferred embodiments, the various components of the detection apparatus may conveniently be made of molded plastic parts, or may be made of any other suitable material.

In some preferred embodiments, the detection apparatus may have a plane that enables the whole apparatus to be in a stationary state when it is placed horizontally. The term "stationary state" means that it does not roll arbitrarily. Since the detecting element may be flat, it needs to be laid flatly for testing. At this time, ensure that it does not roll after placement, affecting the detection. In some preferred embodiments, the detection apparatus may have at least one of the above planes. In some preferred embodiments, the outer wall of the detection apparatus may be composed of at least three of the above planes.

Figure 2:
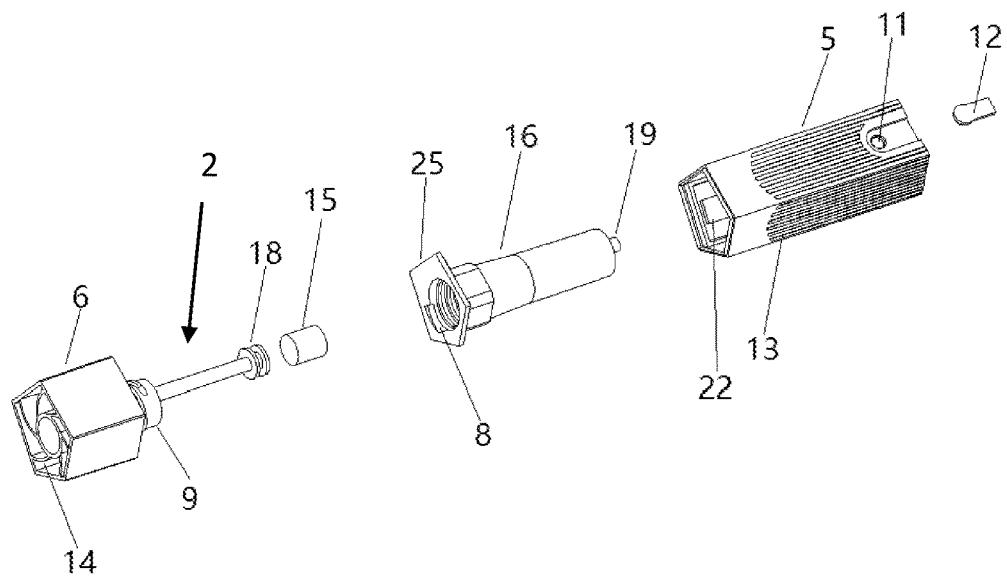
FIG. 2 is an exploded view of the apparatus of the present invention.

FIG. 2 shows a sample collector and a sample receiving cup 1. In the embodiment, the sample collector 2 comprises a collecting element 15 for collecting a liquid sample, and a push rod 17 for fixing the collecting element 15. The sample receiving cup comprises a cup body 5, and the cup body 5 is fixedly connected with a sleeve 16 for cooperating with the collecting element 15, and the sleeve 16 is capable of receiving and holding the sample collector.

In some preferred embodiments, the collecting element 15 is compressible, by which it compresses or rebounds to squeeze or draw samples. In some preferred embodiments, the collecting element 15 is fixedly mounted on the sample collector by a connector, and in some preferred embodiments, the collecting element 15 is detachably connected to the sample collector. In some preferred embodiments, the sample collector is provided with a component for connecting the collecting element 15, and the component may be a connecting rod, such that the collecting element can be inserted into the sample collector to place samples after samples are collected.

For example, the sample collector absorbs a liquid sample using a compressible collecting element 15, here, the "compressible" means that the shape of the material can be deformed by mechanical pressure to squeeze the liquid from the material as it remains. The collecting element 15 can be made of any material that absorbs and retains liquid. In some embodiments, the collecting element is a sponge, but in other embodiments, it may be a nonwoven, absorbent paper, nylon, cotton or any other material that can absorb and retain liquids. When the collecting material 15 is a sponge, it may be natural or synthetic. In this embodiment, as shown in FIG. 2, the collecting element 15 is a cylindrical sponge material suitable for being placed in a subject's mouth to collect saliva. But in other embodiments, the collecting element 15 may be in any suitable and convenient shape. In a special embodiment, the collecting element 15 is treated with a chemical component (for example, a citrate or other chemicals) to promote salivation and facilitate absorption by the collecting element 15.

Figure 3:
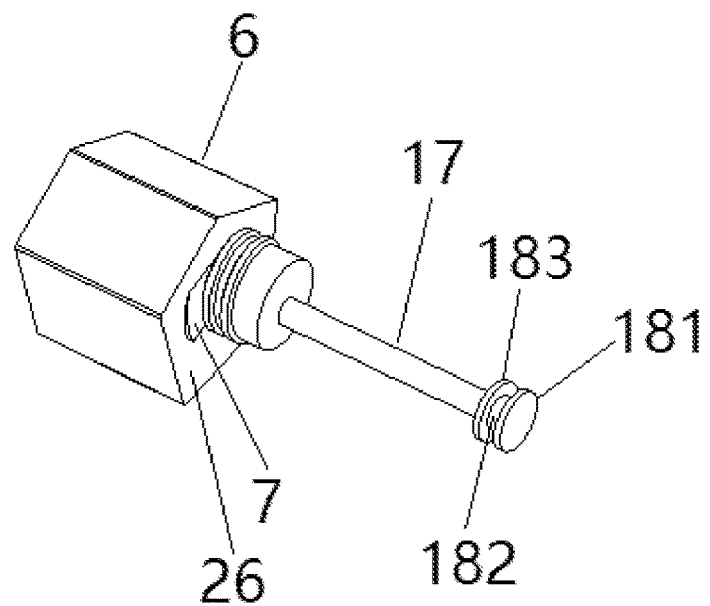
FIG. 3 is a schematic structural view of a fixing base of the apparatus of the present invention.

In the illustrated embodiment, as shown in FIG. 2, the collecting element 15 is connected to the connector 18 at one end of the push rod 17, and in some preferred embodiments, the collecting element 15 is detachably connected to the connector 18. In other embodiments, the collecting element 15 is fixedly connected to the connector 18. In some preferred embodiments, the collecting element 15 can be attached or welded to the collector 18 of the push rod 17 by a sealant or a hot melt adhesive or other adhesives. In some preferred embodiments, the connector 18 has a sealing structure, for example, a sealing ring. The sealing structure on the connector 18 can fit the inner wall of the sleeve 16 and ensure that the samples collected will not flow back when the connector 18 is pressed down. In the illustrated embodiment, as shown in FIG. 3, the connector 18 comprises a head portion 181, a middle portion 182, and an end portion 183. In some preferred embodiments, the collecting element 15 is connected to the end face of the head portion 181. In some preferred embodiments, the collecting element 15 may also be connected to the middle portion 182. In some preferred embodiments, the collecting element 15 may also be connected to the end portion 183. In some preferred embodiments, the collecting element 15 is closer to the head portion 181 of the connector 18 than the sealing structure. In some preferred embodiments, the sealing structure is connected to the middle portion 182 of the connector, and the collecting element 15 is connected to the end face of the connector head portion 181. In some preferred embodiments, the sealing structure is connected to the end portion 183 of the connector.

The push rod 17 is connected to the fixing base 6 at one end away from the connector. The cross-sectional area of the fixing base 6 is larger than the cross-sectional area of the push rod, so the fixing base is disposed to facilitate operators to grab the sample collector. The push rod 17 and the fixing base 6 may be fixedly connected by integral molding or by other suitable means, for example, by snapping, or by bonding or cooperation of internal and external threads. In the illustrated embodiment, as shown in FIGS. 2-3, the fixing base 6 covering surface has a cylindrical protrusion 9. The fixing base covering surface 26 refers to a contact surface in contact with the upper surface of the sleeve 16 when the fixing base covers the sleeve 16. The push rod is fixedly connected to the cylindrical protrusion 9 by integral molding. The periphery of the cylindrical protrusion 9 is provided with an external thread. In some embodiments, the fixing base 6 is provided with an internal thread for detachably connecting the sleeve 16. In some embodiments, the fixing base 6 is provided with other suitable structures for detachably connecting the sleeve 16, for example, a buckle structure or other parts that fit snugly and hold the two members together.

The fixing base 6 can completely cover the sleeve 16, and the term "completely cover" herein means that, when fixing base 6 completely covers the sleeve 16, a sealing structure is formed, and liquid samples cannot leak through the cover from the apparatus. In the process of completely covering the sleeve by the fixing base 6, the collecting element 15 is constantly compressed.

A positioning convex portion or a positioning concave portion is disposed on the covering surface 26 of the fixing base. The positioning convex portion or the positioning concave portion is disposed on the covering surface 26, without affecting the external structure of the fixing base 6 or the cup body 5, and the structure outside the apparatus will not affect the positioning of the apparatus. The positioning convex portion may be a positioning block 7, and the positioning concave portion may be a positioning groove 8. In the illustrated embodiment, as shown in FIGS. 2-3, an arc-shaped positioning block 7 is provided on the fixing base covering surface 26, and the arc-shaped positioning block 7 is connected to the end of the external thread of the cylindrical protrusion, such that the arc-shaped positioning block 7 is smoothly screwed into a corresponding positioning groove for positioning after the external thread is screwed completely.

In the illustrated embodiments, a reinforcing structure 14 is provided on the inner wall of the fixing base 6 for reinforcing the sidewall of the fixing base, so that the fixing base 6 is more firm and stable and is not easily damaged. As shown in FIG. 1, the reinforcing structure 14 is a blade-shaped structure which has good reinforcing effect. The fixing base 6 is firm and is not easily damaged, with an attractive appearance. In other embodiments, the reinforcing structure 14 can be a plate or any other suitable structure.

In the illustrated embodiments, as shown in FIG. 2, the sleeve 16 has an inner cover 25 at one end, the inner cover 25 can cover the cup body 5 opening, and the inner cover 25 is provided with opening to facilitate the insertion of the collecting element 15 into the sleeve 16. The sleeve 16 has a closed surface 27 at the other end, and the closed surface 27 closes the other end of the sleeve 16. A nozzle 9 is provided at the eccentric position of the closed surface 27, to facilitate the flow of the liquid sample from the nozzle 19 after being compressed. The sleeve 16 is tapered, the inner cover 25 opening has an inner diameter larger than the diameter of the closed surface 27, and the diameter of the closed surface 27 is larger than the outer diameter of the nozzle 19. The inner cover 25 opening has an inner diameter larger than the maximum cross-sectional width of the collecting element 15, and the diameter of the closed surface 27 is larger than the minimum cross-sectional width of the collecting element 15. After collecting the liquid sample, the collecting element 15 is inserted from the inner cover opening into the sleeve 16, and in the process of continuous insertion into the sleeve 16, the collecting element 15 is not only subjected to the thrust of the push rod 17, but also the squeezing of the inner wall of sleeve 16 on the periphery, so that the liquid sample can be quickly and completely removed from the collecting element 15. In other embodiments, the sleeve 16 may also be in other shape that matches with the shape of the collecting element 15.

The inner cover 25 of the sleeve 16 is fixedly connected to the cup body 5 and may be attached or welded to the opening end of the cup body 5, or may be fixed by other suitable means. In the illustrated embodiment, as shown in FIG. 2, an internal thread that matches with the external thread of periphery of the fixing base protrusion 9 at the opening of the sleeve inner cover 25. The upper surface of the sleeve inner cover 25 is provided with an arc-shaped positioning groove 8 that cooperates with the arc-shaped positioning block 7 on the covering surface 26 of the fixing base.

By rotating the fixing base 6, the external thread on the fixing base 6 is continuously screwed into the internal thread at the inner cover 25 opening until the inner cover 25 is completely covered and the arc-shaped positioning block 7 is also completely screwed into the arc-shaped positioning groove 8. The arc-shaped positioning block 7 cooperates with the arc-shaped positioning groove 8 to limit the movement of the fixing base 6 in the tightening direction, but allow the fixing base 6 to move in the opposite direction under the action of the external force to open the fixing base 6. The setting of the positioning block 7 and the positioning groove 8 makes operators to feel completely covering the inner cover 25 by the fixing base 6, to avoid tightening the fixing base 6 with a great force after the inner cover 25 is tightened and covered, which may easily damage the fixing base 6; in addition, as operators are not sure whether to tighten, they may tighten the fixing base for multiple times, which wastes the time and affects the operation efficiency. After the rotation is completed, the fixing base 6 completely covers the sleeve 16 opening to form a sealing structure. The liquid sample cannot leak from the apparatus through the cover, and the positioning block 7 is screwed into the positioning groove to give a rotation indication, so that operators can clearly know that the apparatus has been completely covered and there is no need to tighten the fixing base 1. During the rotation, by squeezing the collecting element 15 that has absorbed liquid samples, the liquid samples on the collecting element 15 are squeezed from the nozzle 19 into the sample receiving cup 1.

The sample receiving cup 1 comprises a cup body 5, as shown in FIGS. 1-2, the fixing base 6 in the sample collector can cover the inner cover 25, and then cover the cup body 5, and the fixing base 6 can tightly cover the cup body 5, after the fixing base 6 completely covers the cup body 5, it becomes a whole, which is transported, carried, used, stored or discarded as a whole.

The cup body 5 and/or the fixing base 6 may be in the shape of a polyhedron. The fixing base 6 and the cup body 5 are both polyhedral shapes, that is, the fixing base 6 and the cup body 5 may have polygonal cross sections, which may be triangles, quadrangle, pentagons or other polygons, or may be regular polygons or non-regular polygons. One or more detecting elements 10 may be disposed in the cup body 5 of the polyhedron shape to detect different analytes in the sample simultaneously. The detecting element 10 may be disposed on any of the side inner wall of the polyhedron cup body, and any of the side inner walls of the cup body 5 may be provided with a placement portion 22 for placing the detecting element. As shown in FIG. 2, in the illustrated embodiment, the cup body 5 is an irregular pentahedron, that is, the cup body 5 has an irregular pentagon shape in cross section, wherein the inner wall of the side surface of the pentahedron cup body with the maximum area is provided with a detecting element placement portion 22 for placing detecting element 10. The inner cover 25 has the same shape and side length as those of the cross section of the cup body 5, and it is also an irregular pentagon shape. Therefore, the inner cover 25 can tightly cover the opening of the cup body 5, and each side of the inner cover does not extend beyond the side of the cup body 5, so that the cup body 5 can be placed horizontally and stably on the side.

The fixing base 6 and the cup body 5 may be polyhedrons having the same number of faces, or polyhedrons having different numbers of faces. In the illustrated embodiment, both the fixing base 6 and the cup body 5 are irregular pentahedrons. After the fixing base 6 completely covers the cup body 5, the fixing base 6 with the largest area is aligned with one side of the cup body with the largest area, so that it is convenient for confirming that the fixing base 6 has completely covered the cup body 5. The cross section of the fixing base 6 is close to the side length of the pentagon of the cup body 5 cross-section. When the fixing base 6 completely covers the cup body 5, each side of the fixing base 6 is nearly flush with each side of the cup body 5, almost at the same plane, so that the fully covered apparatus can be placed flatly on the side to facilitate scanning of the test results.

In the illustrated embodiment, the cup body 5 is made of a transparent material, to facilitate the observation of test results.

In the illustrated embodiment, a secondary sampling port 11 is provided on one side of the cup body 5. As shown in FIG. 2, a lower part of one side of the cup body 5 is provided with an arch-shaped recessed portion, and a secondary sampling port 11 is disposed at the arch-shaped recessed portion. The plug 12 can block the secondary sampling port 11. After the plug 12 blocks the secondary sampling port 11, the side with the secondary sampling port 11 can still be placed flatly on the side. In some embodiments, the secondary sampling port 11 may be capped with a plug 12 during the sample testing and the apparatus transport for sealing. When the apparatus is received on the clinical test equipment, the plug 12 can be removed and users can take out samples from the secondary sampling port 11 for second confirmatory detection. The setting of the secondary sampling port 11 allows users to add solvent or other required substances from the secondary sampling port, for example, adding solvent. The addition of solvent increases the amount of liquid sample, and the sample solution is diluted or the solvent that can lower the viscosity of a liquid sample can be added. In some embodiments, operators can conveniently take the samples using a straw or other sampling device when the plug 12 is opened. The sample receiving cup 1 can be conveniently held in a closed state, and liquid sample is still allowed to be taken out.

In the illustrated embodiment, an anti-slip structure 13 is provided on the outer side of the cup body 5. As shown in FIG. 1, the anti-slip structure 13 is a rib, the setting of the rib makes users to easily hold or grasp the sample receiving cup 1, and avoid slipping and falling to damage the sample receiving cup 1. In some embodiments, the outer side of the cup body 5 is provided with other anti-slip structures 13, for example, a pit or any other suitable structure.

Figure 5:
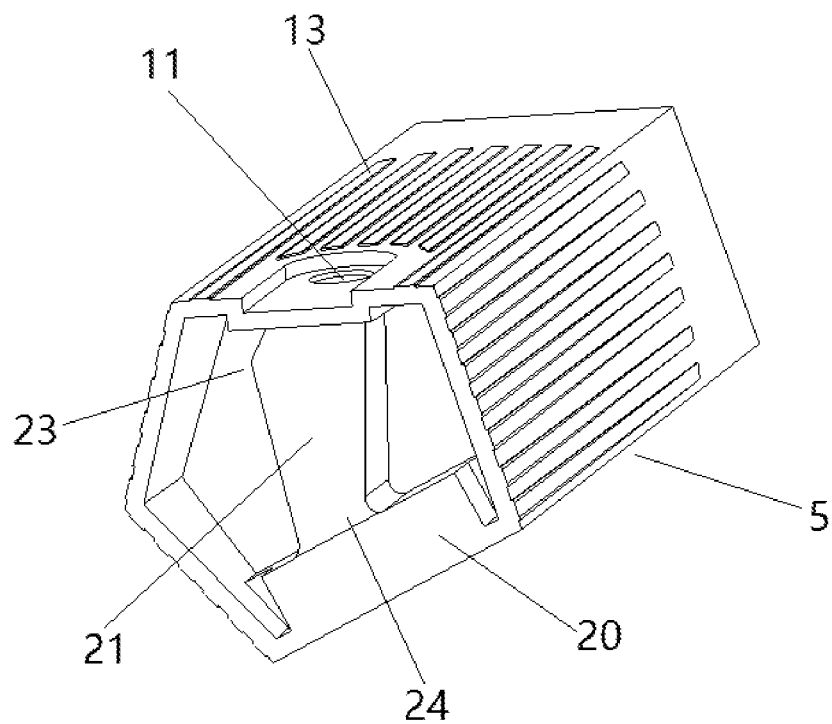
FIG. 5 is a schematic view of a bottom structure of the apparatus of the present invention.

In the illustrated embodiment, as shown in FIGS. 2 and 5, a sample receiving cup 1 is provided with a first receiving area 20 for receiving and storing a sample; and the sample receiving cup 1 is further provided with a flow-guiding channel 121 through which a sample can be added or collected; the first receiving area 20 is in communication with the flow-guiding channel 121, so that the samples can move between them. The first receiving area 20 and the flow-guiding channel 21 are both disposed at the bottom of the cup body 5.

Figure 6:
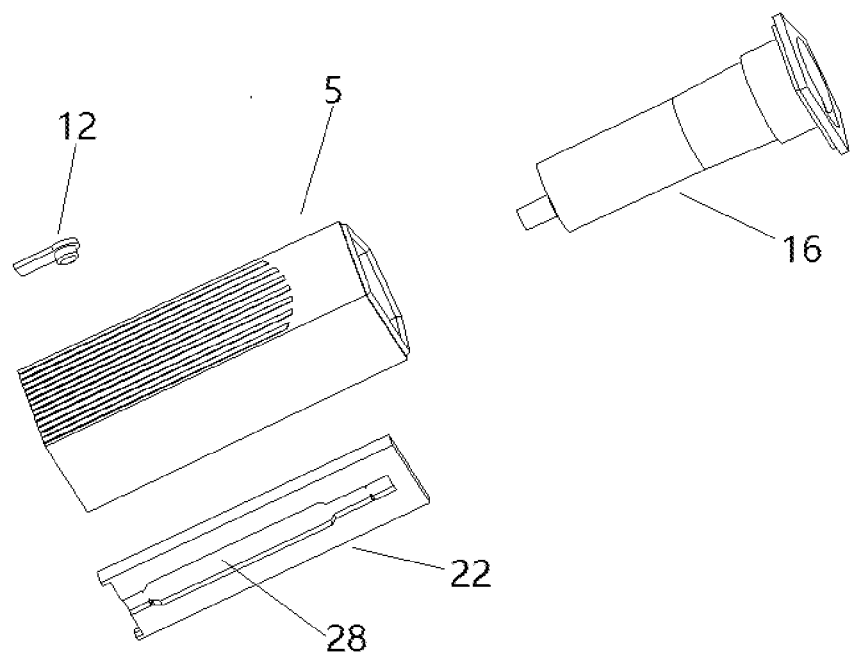
FIG. 6 is an exploded view of a sample receiving cup of the present invention.
Figure 7:
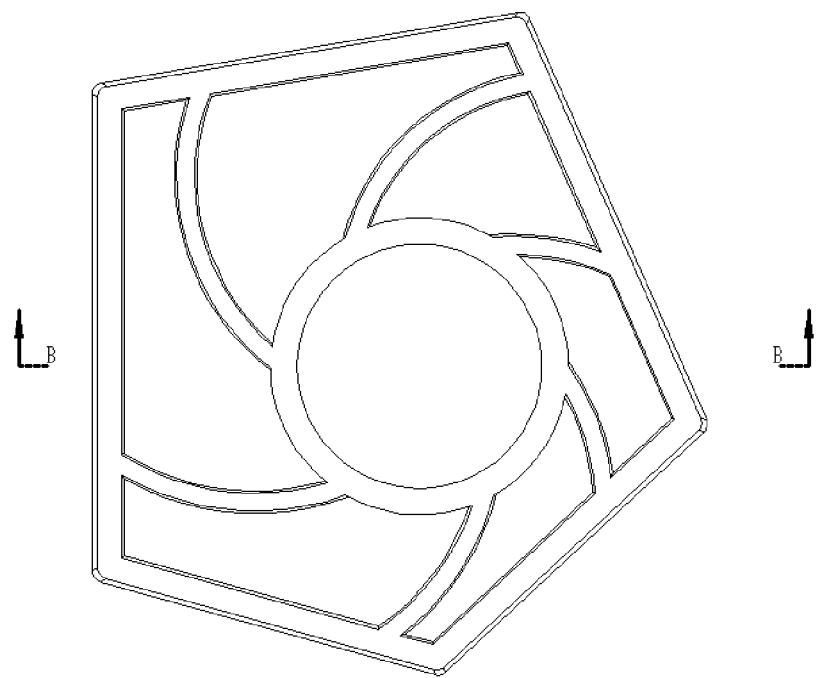
FIG. 7 is a top view of the apparatus of the present invention in an assembled state.
Figure 8:
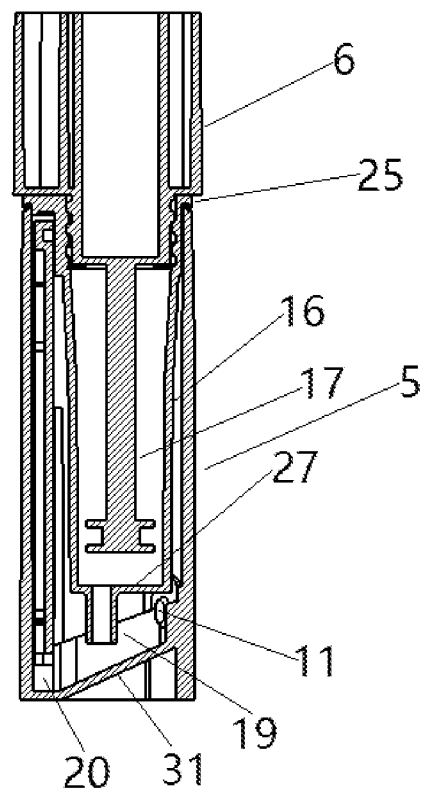
FIG. 8 is a cross-sectional view of the B-B direction of FIG. 7 (the collecting element is hidden in the figure).

The sample receiving cup 1 may comprise at least one detecting element for detecting the presence or amount of analyte in a sample. The detecting element may be distributed on the inner wall of one side of the apparatus herein, or the inner walls of a plurality of sides of the apparatus herein. The inner wall of the side of the cup body 5 is further provided with a placement portion 22 for placing a detecting element, and the detecting element may be placed in the placement portion 22. The placement portion 22 is connected to the side inner wall of the cup body. The placement portion 22 is detachably connected to the inner wall of the side of the cup body. In some preferred embodiments, the placement portion 22 may be a detection plate. In some preferred embodiments, the placement portion 22 may be provided with a slot 28, in some preferred embodiments, the detecting element may be a strip or similar strip, and these strips or similar strips may be placed in the slot 28. In some preferred embodiments, one slot 28 can be disposed on one detection plate, and in some other preferred embodiments, a plurality of slots 28 can be disposed on one detection plate. In the illustrated embodiment, as shown in FIGS. 6 and 8, the cup body 5 is an irregular pentahedron, that is, the cup body 5 has an irregular pentagon in cross section. The placement portion 22 can be inserted into the cup body 5, the placement portion 22 is closely attached to the side of the cup body having the largest area, and the side surfaces adjacent to the largest side of the cup body are provided with a blocking strip 30, and the plane of the blocking strip 30 is parallel to the side with largest area. The blocking strip 30 can block the placement portion 22, so that the placement portion 22 is stably placed in the cup body 5, avoiding the placement portion 22 from shaking in the cup body 5, but allowing the placement portion 22 to be inserted into a space between the blocking strip 30 and the side with the largest area. In the illustrated embodiment, a slot 28 is provided on the placement portion 22.

The "detecting element" may be any test device that provides a test result. In some embodiments, the detecting element is a test strip, and the test strip may have specific binding molecule immobilized thereon and a reagent for immunoassay. But in other embodiments, the detecting element may also be a chemical reaction-based test reagent, a biological-based test reagent (e.g., an enzyme assay or ELISA assay), or a fluorescent test reagent, etc. Moreover, in some other embodiments, there are some other reagents on the detecting element, and these reagents can be used to detect the presence or amount of an analyte in the sample. In some embodiments, the detecting element comprises an agent for detecting the presence of drug abuse. However, in other embodiments, the detecting element can be any component that provides an indication of the test result. For example, some chemical or biological indicator reagents can be used.

When the detecting element is a test strip, it may comprise a water absorbing matrix (e.g., nitrocellulose) and/or other suitable materials. The matrix may have a sample loading area, a reagent or a labeled area and a detection area. These types of test strips are well known in the art, and those of ordinary skill in the art will recognize various test strips that can be used in the present invention with reference to the present disclosure. In some embodiments, the sample loading area is located at one end of the test strip to apply the samples to the test strip. The reagents used to perform the assay or to adjust the sample may also be located in the sample loading area, or they may be located in separate reagent area or labeled area on the test strip. These reagents can be used for a variety of purposes, for example, for preparing a sample for achieving the desired binding to a particular binding molecule, or improving the stability of the analyte of interest.

The sample in which the analyte is detected in the present invention may be any fluid sample. Fluid samples suitable for testing using the present invention include oral fluid, saliva, whole blood, serum, plasma, urine, spinal fluid, biological extracts, mucus, and tissues. "Saliva" refers to the secretions of the salivary glands. "Oral fluid" refers to any fluid present in the oral cavity.

The analyte to be detected can be any analyte, and the detecting element can be made for the analyte. In one embodiment, the analyte is a drug of abuse. Other examples of analytes of interest include hormones, proteins, peptides, nucleic acid molecules, pathogenic agents, and specific binding components. "Drug of Abuse (DOA)" is a drug used for non-medical purposes (usually for psychedelic effects). The abuse of these drugs may cause harm to the body and metal state and (in some cases) may cause dependence, addiction and even death. Examples of DOA include cocaine, amphetamines (e.g., black beauties, white bennies, amphetamines, dextroamphetamine, dexies, beans), methamphetamines (crank, methamphetamine, crystal, speed), Barbiturates (Roche Pharmaceuticals, Nutley, New Jersey), sedative medications (e.g., hypnotics), lysergic acid diethylamide (LSD), sedatives (downers. goofballs. barbs. blue devils. yellow jackets. ludes), tricyclic antidepressants (TCA, such as imipramine, amitryptyline and doxepin), phencyclidine (PCP), tetrahydrocannabinol and opiates (e.g., morphine, opium, codeine, heroin).

In the illustrated embodiments, as shown in FIG. 5, the first receiving area 20 is disposed at the lower part of the detecting element. The liquid sample in the first receiving area 20 can reach the detecting element, so that the detecting element can detect the sample. In some embodiments, the absorbent material absorbs the liquid sample of the first receiving area 20 and delivers it to the detecting element, providing a fluidic communication between the first receiving area 20 and the detecting element such that the absorbent material will not absorb and transport more liquid samples than the amount that can be loaded on the detecting element, to cause an overflow on the detecting element. A "fluidic communication" structure means that fluid from one structure will encounter another structure that is in fluidic communication therewith. Thus, when the first receiving area 20 is in fluidic communication with the detecting element, the liquid sample of the first receiving area 20 reaches the detecting element through the absorbent material. The first receiving area 20, the absorbent material, and the detecting element may be in direct physical contact, or there may be gaps between them but remain in fluidic communication. An "absorbent material" is a material that absorbs liquid and can transport liquid by capillary action. Absorbent materials include, but are not limited to, filter paper or other types of absorbent paper, specific nylons, nitrocellulose, and other materials having such characteristics. In some preferred embodiments, there may be no absorbent material, and the fluidic communication between the first receiving area 20 and the detecting element can be maintained.

The flow-guiding channel 21 is connected to the first receiving area 20 and the other side inner wall of the cup body 5. As a preferred embodiment, this side is the side where the secondary sampling port 11 is located. The flow-guiding channel 21 may be a groove, the groove comprises a bottom surface 31 and a sidewall 32, and provides a passage for the liquid samples. A second receiving area is provided in the groove, and the second receiving area is connected to the side inner wall of the cup body 5. The setting of the groove facilitates the flow-guiding and collection of liquid samples, avoiding the liquid samples from flowing to a large area randomly, which is not conducive to collecting the liquid sample for second detection; and avoiding waste of the liquid sample, especially for liquid samples with poor fluidity and/or very small size, the setting of the groove is very important, which avoid a large area of retention of liquid samples with poor fluidity and/or very small size in the bottom of the cup body, causing difficulty or failure to collect, and unable to perform a second detection.

When squeezed from the nozzle 19 of the sleeve 16, the liquid sample flows into the first receiving area 20 along the groove bottom surface 31, and after the liquid sample is squeezed from the nozzle 19, it is subjected to momentum, such that the liquid sample can be quickly collected in the first receiving area 20 without being retained in a contact surface where the liquid is in contact with. For liquid samples with poor fluidity and/or small sample size, this downward force of the liquid sample is critical to allow the liquid samples of poor fluidity and/or small sample size to reach the first receiving area 20 smoothly, to complete the detection. The liquid sample is squeezed from the nozzle 19, and then flows into the first receiving area 20 along the bottom surface 31 of the groove, the bottom surface 31 of the groove is set to a slope, and the first receiving area 20 is at the low end of the slope. In this way, the liquid samples can be smoothly flowed into the first receiving area 20, which can effectively prevent the liquid samples with poor fluidity and/or small sample size from staying on the contact surface contacting the liquid, affecting the detection of the liquid samples. If the groove bottom surface 31 is set to a plane, after liquid sample is squeezed from the nozzle, the liquid samples are subjected to a downward force and flow along the plane. A part of liquid samples will flow to the first receiving area 20, but another part of liquid samples will flow along the groove to the other end of the groove, that is, part of liquid samples cannot flow directly to the first receiving area 20, which will lose the small amount of valuable sample for liquid samples with poor fluidity and/or small sample size. In summary, the liquid sample is squeezed from the nozzle, and subjected to a force; moreover, the groove bottom surface 31 is set to a slope, which facilitates the flow of the liquid samples into the first receiving area 20. It is a preferred embodiment.

Figure 4:
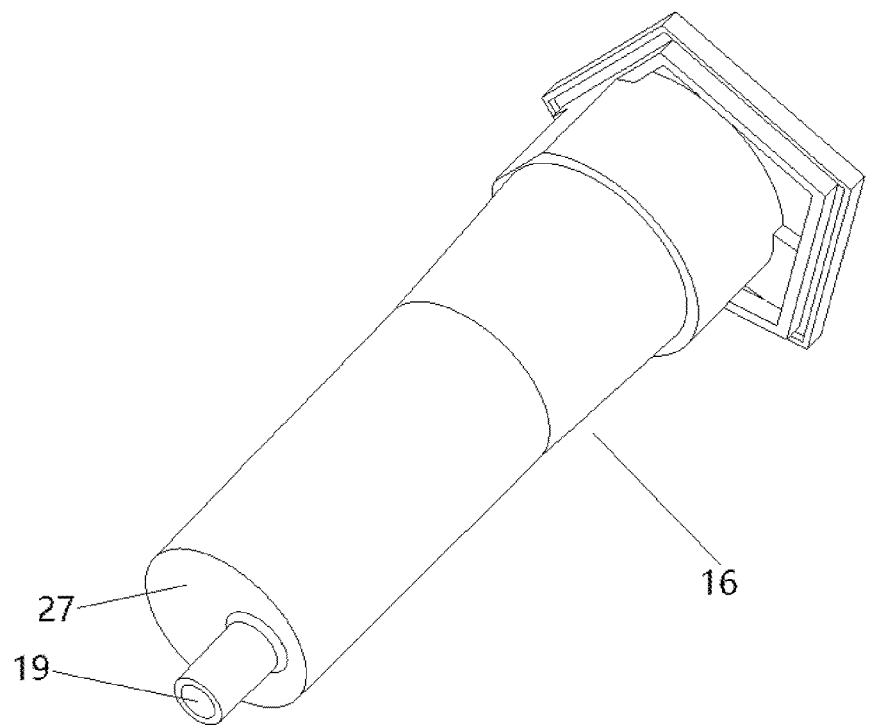
FIG. 4 is a schematic structural view of a sleeve of the apparatus of the present invention.

In the illustrated embodiment, as shown in FIG. 4 and FIG. 8, the nozzle 19 is disposed in the eccentric position of the closed surface 27. The nozzle 19 extends into the groove, but does not touch the groove bottom surface, such that liquid samples are in contact with the groove bottom surface 31 after squeezed out of the nozzle. The sidewall 32 of the groove can block part of the liquid sample from splashing from the groove and then liquid samples flow into the first receiving area 20 along the groove bottom surface 31. The nozzle is closer to the groove inlet 24, so the nozzle 19 is closer to the first receiving area 20, so that the flow path of the liquid sample is the shortest, to reach the first receiving area 20 quickly. For liquid samples with poor fluidity and/or very small size, it can effectively avoid the waste and loss. In the illustrated embodiment, as shown in FIG. 5, the bottom surface 31 of the groove is set to a slope, the groove inlet 24 is lower than the groove outlet, and the groove inlet 24 is connected to the first receiving area 20. The first receiving area 20 is disposed at a lower part of the detecting element, and the outlet of the groove is connected to an opposite side of the detecting element side, the opposite side herein means a cup body side not adjacent to the side of the detecting element, and the side is the side where the secondary sampling port is located. The liquid sample of the first receiving area 20 can enter the groove from the groove inlet 24 and flow along the groove to the second receiving area.

In some embodiments, the second receiving area may comprise a corner area 29, which is used to collect samples for secondary sampling. In the illustrated embodiment, as shown in FIGS. 5 and 8, a sidewall 32 of the groove is provided with a corner 23, and the corner 23 may be a right angle, a rounded corner, a chamfer, a sector angle and other suitable shapes. The corner 23 is arranged to facilitate the collection of liquid samples, to facilitate to collect and draw liquid samples.

When secondary sampling is required, the liquid in the first receiving area first flows into the second receiving area, but sampling is usually performed by a straw, or a pipette, or a gun. As the sample size collected is small, it is not easy to extend the straw into the first receiving area. Generally the first receiving area 20 is a planar structure, and the first receiving area 20 is far from the secondary sampling port 11, so the sampling tube cannot reach the first receiving area 20 when it is not long enough. In addition, the sample size is small, and it is not easy to draw enough samples. In the present invention, a corner area 29 is provided near the secondary sampling port 11. When sampling is required, the cup body structure is slightly tilted, to allow samples to flow from the first receiving area 20 to the corner area 29 through the groove. At this time, it is convenient to insert a straw from the secondary sampling port 11 and easy to reach the corner area to draw samples. As the corner area has the function of collection and even if the sample size is small, enough samples can be collected for secondary sampling.

Figure 9:
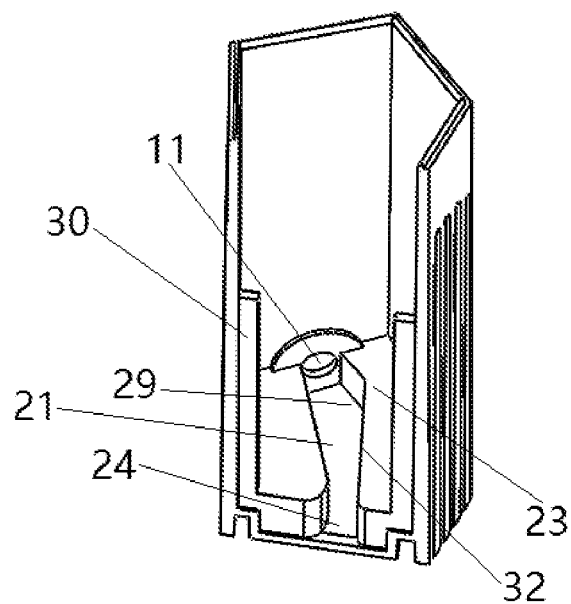
FIG. 9 is a schematic diagram of the internal structure of the sample receiving cup body of the present invention (in order to clearly show the structure of the flow-guiding channel, one side of the cup body is hidden).

In some embodiments, as shown in FIG. 9, the corner area 29 is not directly facing but deviates from the secondary sampling port 11. The "deviate" means that the corner area 29 is not on the same line as the central axis of the secondary sampling port 11, but deviates from the central axis, by this way, the straw is inserted obliquely through the secondary sampling port 11 to reach the corner area 29 for sampling.

In some embodiments, the outlet of the groove is connected to the secondary sampling port 11, the secondary sampling port 11 is located at the upper part of the outlet of the groove. Further, the outlet of the groove is overlapped with the secondary sampling port 11. In the illustrated embodiment, half of the area of the secondary sampling port 11 overlaps with the groove outlet, the secondary sampling port 11 cooperates with the corner area 29 to facilitate the insertion of the sucking device to the secondary sampling port 11 to take liquid samples from the corner area 29 for second detection or other purposes, or a solvent or other desired substance may be added from the secondary sampling port. For example, adding a solvent increases the size of liquid samples, diluting liquid samples or adding a solvent that lowers the viscosity of liquid samples.

The present invention further provides a method of using the apparatus for detecting an analyte in a liquid sample, which is described with reference to the embodiment of FIGS. 1-9. The collecting element 15 of the sample collector is placed in the mouth of a user, and the collecting element 15 continuously absorbs the saliva, then the collecting element 15 is taken out of the user's mouth and put into the sleeve 16 used with the collecting element 15. The fixing base 6 is rotated until the sleeve 16 opening is completely covered, the liquid sample cannot leak from the apparatus through the cover, and the positioning block 7 is screwed into the positioning groove to give a rotation indication. During the rotation, by squeezing the collecting element 15 that has absorbed liquid samples, the liquid samples on the collecting element 15 are squeezed from the nozzle 19, and liquid samples flow from the bottom surface 31 of the groove to the inlet 24 of the groove, and to the first receiving area 20, and the liquid sample of the first receiving area 20 reaches the detecting element, which is detected on the detecting element. After a period of time for testing, the presence and amount of the analyte in the liquid sample is determined. When a second confirmatory detection is required, the plug 12 is opened and the sample receiving cup 1 is tilted. The remaining liquid sample in the first receiving area 20 enters the groove from the groove inlet 24 and flows along the groove and is collected in the corner area 29. The sampler can be inserted from the secondary sampling port 11 to the liquid sample of the corner area 29, to draw liquid samples, which are reserved for second confirmatory detection.

Example 2

Figure 10:
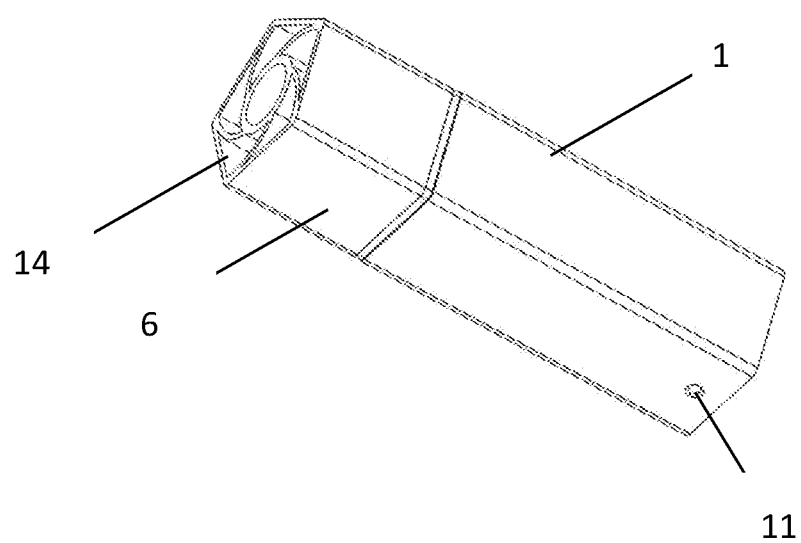
FIG. 10 is a schematic structural view of an apparatus according to another embodiment of the present invention.

As shown in FIG. 10, the present invention provides an apparatus for detecting the presence or amount of an analyte in a liquid sample, the detecting device being in an assembled state. The detection apparatus may comprises a sample collector 2 and a sample receiving cup 1, the sample collector 2 is used to directly or indirectly collect samples from a patient's body or a site to be collected or in a scene that is separated from a patient's body.

The sample receiving cup 1 can receive and hold the sample collector 2, and in some preferred embodiments, the sample receiving cup 1 can receive the sample collector 2 itself or a part thereof. After collecting samples, the sample collector 2 can be put into the sample receiving cup 1, and then the sample is transferred to the sample receiving cup 1; in some preferred embodiments, the sample receiving cup 1 can directly receive the samples collected by the sample collector.

In some preferred embodiments, the sample receiving cup comprises at least one detecting element 3 for detecting the presence or amount of an analyte in a sample.

Figure 11:
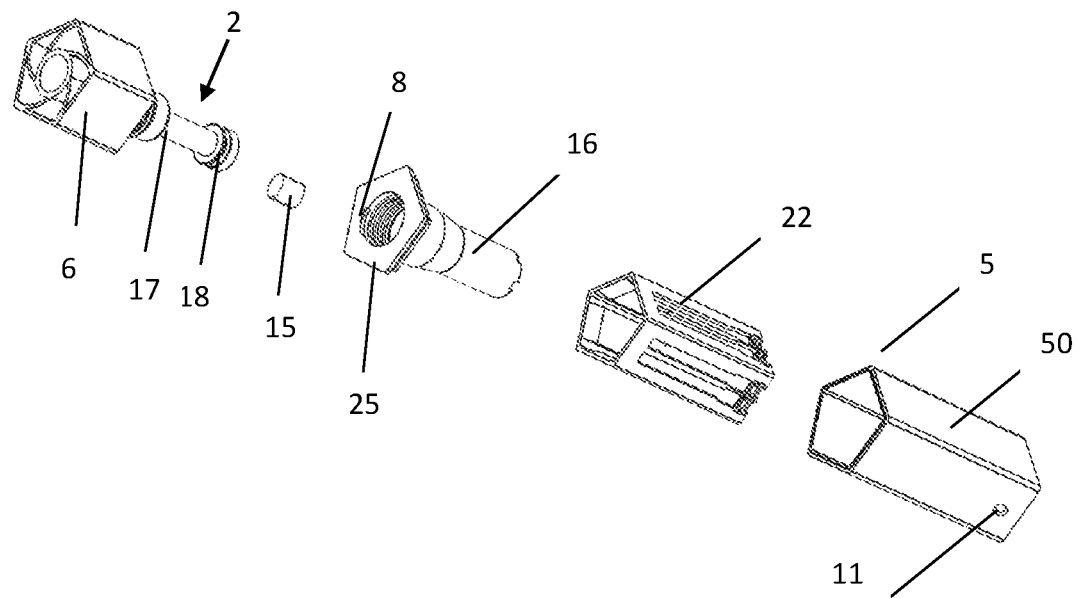
FIG. 11 is an exploded view of an apparatus according to another embodiment of the present invention.

FIG. 11 shows the sample collector 2 and the sample receiving cup 1. In some preferred embodiments, the sample collector 2 comprises a collecting element 15 for collecting a liquid sample and a push rod 17 for fixing the collecting element 15. In some preferred embodiments, the apparatus further comprises a sleeve 16 for use with the sample collector 2, the interior space of the sleeve 16 is capable of receiving and holding a sample collector 2 that is fixedly or detachably connected to the sample receiving cup 1. In some preferred embodiments, the sample receiving cup comprises a cup body 5, and the cup body 5 comprises a sidewall 50, and the sleeve 16 is fixedly or detachably connected to the cup body 5. In some preferred embodiments, the sample receiving cup 1 and the sleeve 16 have the same round mandrel, and the cross-sectional area of the sample receiving cup 1 is larger than the cross-sectional area of the sleeve 16. When the sleeve 16 is disposed in the sample receiving cup 1, the area between the cup body 5 of the sample receiving cup 1 and the sleeve 16 is a space in which the detecting element 3 is placed.

In some preferred embodiments, the collecting element 15 is compressible, by which it compresses or rebounds to squeeze or draw samples. In some preferred embodiments, the collecting element 15 is fixedly mounted on the sample collector 2 by a connector, and in some preferred embodiments, the collecting element 15 is detachably connected to the sample collector 2. In some preferred embodiments, the sample collector 2 is provided with a component for connecting the collecting element 15, and the component may be a connecting rod, such that the collecting element can be inserted into the sample collector to place samples after samples are collected.

The sample collector absorbs the liquid sample using a compressible collecting element 15, as shown in FIG. 11, the collecting element 15 is a cylindrical sponge material suitable for being placed in a subject's mouth to collect saliva. But in other embodiments, the collecting element 15 may be in any suitable and convenient shape. In a special embodiment, the collecting element 15 is treated with a chemical component (for example, a citrate or other chemicals) to promote salivation and facilitate absorption by the collecting element 15.

Figure 12:
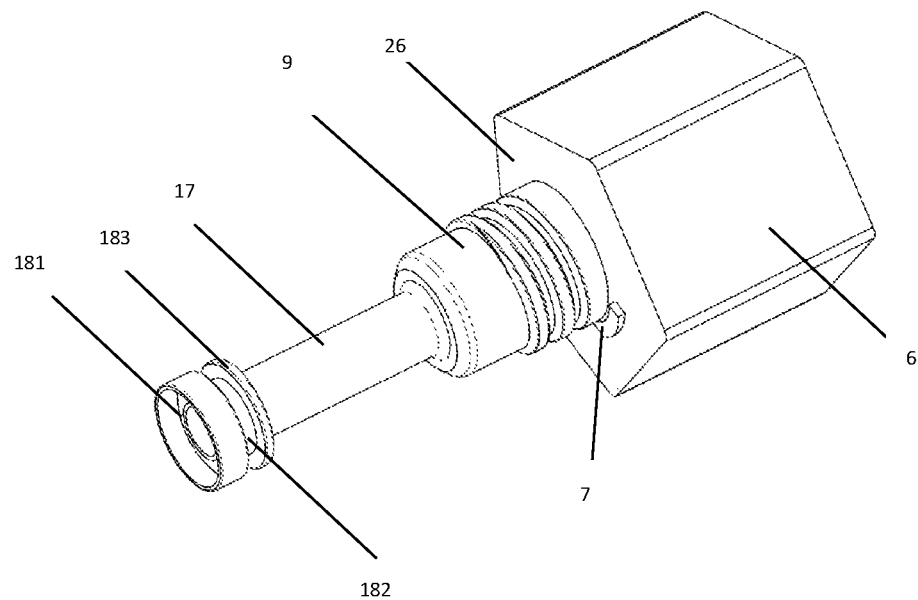
FIG. 12 is a schematic structural diagram of a fixing base of an apparatus according to another embodiment of the present invention.
Figure 13:
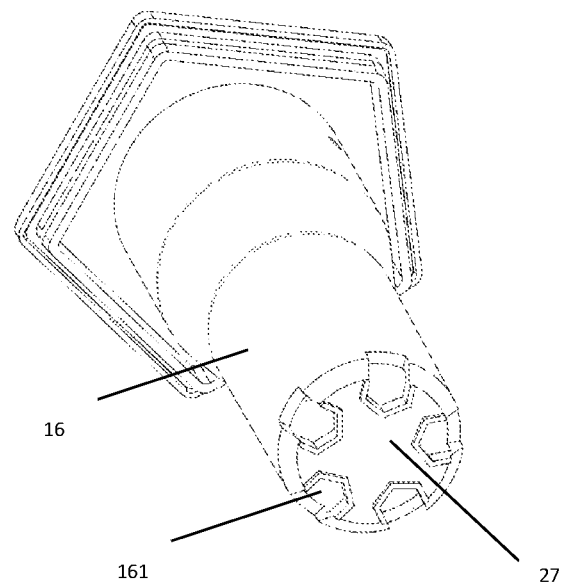
FIG. 13 is a schematic structural view of a sleeve of an apparatus according to another embodiment of the present invention.

In the illustrated embodiment, as shown in FIG. 11, the collecting element 15 is connected to the connector 18 at one end of the push rod 17, and in some preferred embodiments, the collecting element 15 is detachably connected to the connector 18. In other embodiments, the collecting element 15 is fixedly connected to the connector 18. In some preferred embodiments, the collecting element 15 can be attached or welded to the collector 18 of the push rod 17 by a sealant or a hot melt adhesive or other adhesives. In some preferred embodiments, the connector 18 has a sealing structure, for example, a sealing ring. The sealing structure on the connector 18 can fit the inner wall of the sleeve 16 and ensure that the samples collected will not flow back when the connector 18 is pressed down. In the illustrated embodiment, as shown in FIG. 12, the connector 18 comprises a head portion 181, a middle portion 182, and an end portion 183. In some preferred embodiments, there is a chamber at the head portion 181 of the connector 18, and the collecting element is fixed in the chamber. In some preferred embodiments, there is no chamber at the head portion 181 of the connector 18, and the collecting element 15 is connected to the end face of the head portion 181. In some preferred embodiments, the collecting element 15 may also be connected to the middle portion 182. In some preferred embodiments, the collecting element 15 may also be connected to the end portion 183. In some preferred embodiments, the collecting element 15 is closer to the head portion 181 of the connector 18 than the sealing structure. In some preferred embodiments, the sealing structure is connected to the middle portion 182 of the connector, and the collecting element 15 is connected to the chamber of the connector head portion 181. In some preferred embodiments, the sealing structure is connected to the connector end portion 183.

The push rod 17 is connected to the fixing base 6 at one end away from the connector 18. The cross-sectional area of the fixing base 6 is larger than the cross-sectional area of the push rod, so the fixing base is disposed to facilitate operators to grab the sample collector 2. The push rod 17 and the fixing base 6 may be fixedly connected by integral molding or by other suitable means, for example, by snapping, or by bonding or cooperation of internal and external threads. In the illustrated embodiment, as shown in FIGS. 11 and 12, the covering surface 26 of fixing base 6 has a cylindrical protrusion 9. The push rod is fixedly connected to the cylindrical protrusion 9 by integral molding. The periphery of the cylindrical protrusion 9 is provided with an external thread. In some embodiments, the fixing base 6 is provided with an internal thread for detachably connecting the sleeve 16. In some embodiments, the fixing base 6 is provided with other suitable structures for detachably connecting the sleeve 16, for example, a buckle structure or other parts that fit snugly and hold the two members together.

The fixing base 6 can completely cover the sleeve 16, and the term "completely cover" herein means that, when fixing base 6 completely covers the sleeve 16, a sealing structure is formed, and liquid samples cannot leak through the cover from the apparatus. In the process of completely covering the sleeve by the fixing base 6, the collecting element 15 is constantly compressed.

A positioning convex portion or a positioning concave portion is disposed on the covering surface 26 of the fixing base. The positioning convex portion or the positioning concave portion is disposed on the covering surface 26, without affecting the external structure of the fixing base 6 or the cup body 5, and the structure outside the apparatus will not affect the positioning of the apparatus. The positioning convex portion may be a positioning block 7, and the positioning concave portion may be a positioning groove 8. In the illustrated embodiment, as shown in FIGS. 11 and 12, an arc-shaped positioning block 7 is provided on the fixing base covering surface 26, and the arc-shaped positioning block 7 is connected to the end of the external thread of the cylindrical protrusion, such that the arc-shaped positioning block 7 is smoothly screwed into a corresponding positioning groove for positioning after the external thread is screwed completely.

In the illustrated embodiments, a reinforcing structure 14 is provided on the inner wall of the fixing base 6 for reinforcing the sidewall of the fixing base. As shown in FIG. 10, the reinforcing structure 14 is a blade-shaped structure which has good reinforcing effect. The fixing base 6 is firm and is not easily damaged, with an attractive appearance. In some embodiments, the reinforcing structure 14 can be a plate or any other suitable structure.

In the illustrated embodiments, as shown in FIG. 11, the sleeve 16 has an inner cover 25 at one end, the inner cover 25 can cover the cup body 5 opening, and the inner cover 25 is provided with opening, i.e. the opening of the sleeve, to facilitate the insertion of the collecting element 15 into the sleeve 16 through the opening. The sleeve 16 has a closed surface 27 at the other end, and the closed surface 27 closes the other end of the sleeve 16 to form a bottom of the sleeve. One or a plurality of notches 161 are provided on the closed surface 27, and the liquid flows out of the sleeve 16 via the notch 161 after the collecting element 15 is squeezed, that is to say, the cup body space of the sample collection cup is in communication with the inner space of the sleeve through the notch 161. The sleeve 16 is tapered, the inner cover 25 opening has an inner diameter larger than the diameter of the closed surface 27. The inner cover 25 opening has an inner diameter larger than the maximum cross-sectional width of the collecting element 15, and the diameter of the closed surface 27 is smaller than the minimum cross-sectional width of the collecting element 15. After collecting the liquid sample, the collecting element 15 is inserted from the inner cover opening into the sleeve 16, and in the process of continuous insertion into the sleeve 16, the collecting element 15 is not only subjected to the thrust of the push rod 17, but also the squeezing of the inner wall of sleeve 16 on the periphery, so that the liquid sample can be quickly and completely removed from the collecting element 15. In some preferred embodiments, there are a plurality of notches 161 on the closed surface 27 of the sleeve 16, and the notches 161 are disposed at the edge of the closed surface 27, that is, it is equivalent to having a plurality of hollow structures at the edge of the closed surface 27, thereby forming a notch 161 capable of flowing out of the liquid at the bottom of the sleeve. In some preferred embodiments, the notch 161 is disposed at a position where the closed surface intersects with the sleeve body sidewall. In some preferred embodiments, the closed surface 27 has a plurality of notches 161, and the plurality of notches 161 are evenly arranged in a scattering manner centering on the center of the closed surface. The shape of the notch is not limited and may be a circular, elliptical, regular or irregular polygon, such as a triangle, a square, a rectangle, a pentagon, etc., as long as the liquid can flow out of the sleeve 16. In some preferred embodiments, the closed surface has five notches 161, and the five notches 161 are uniformly arranged in a scattering shape centering on the center of the closed surface, and the notch 161 is in a pentagon shape.

The inner cover 25 of the sleeve 16 is fixedly connected to the cup body 5 and may be attached or welded to the opening end of the cup body 5, or may be fixed by other suitable means. In the illustrated embodiment, as shown in FIG. 11, an internal thread that matches with the external thread of periphery of the fixing base protrusion 9 at the opening of the sleeve inner cover 25. The upper surface of the sleeve inner cover 25 is provided with an arc-shaped positioning groove 8 that cooperates with the arc-shaped positioning block 7 on the covering surface 26 of the fixing base.

By rotating the fixing base 6, the external thread on the fixing base 6 is continuously screwed into the internal thread at the inner cover 25 opening until the inner cover 25 is completely covered and the arc-shaped positioning block 7 is also completely screwed into the arc-shaped positioning groove 8. The arc-shaped positioning block 7 cooperates with the arc-shaped positioning groove 8 to limit the movement of the fixing base 6 in the tightening direction, but allow the fixing base 6 to move in the opposite direction under the action of the external force to open the fixing base 6. The setting of the positioning block 7 and the positioning groove 8 makes operators to feel completely covering the inner cover 25 by the fixing base 6. After the rotation is completed, the fixing base 6 completely covers the sleeve 16 opening to form a sealing structure. The liquid sample cannot leak from the apparatus through the cover, and the positioning block 7 is screwed into the positioning groove to give a rotation indication, so that operators can clearly know that the apparatus has been completely covered and there is no need to tighten the fixing base 6. During the rotation, by squeezing the collecting element 15 that has absorbed liquid samples, the liquid samples on the collecting element 15 are squeezed from the notch 161 into the sample receiving cup 1. In some preferred embodiments, a plurality of raised ribs is distributed on the arc-shaped positioning block 7 and the arc-shaped positioning groove 8. The arrangement of the ribs can increase the friction between the positioning block 7 and the positioning groove 8 during the covering process, and operators can more clearly feel whether the fixing base 6 has completely covered the inner cover 25.

The sample receiving cup 1 comprises a cup body 5, and the cup body 5 has an opening that enables the sample collector and the sleeve to enter. As shown in FIGS. 10 and 11, the fixing base 6 in the sample collector can cover the inner cover 25 of the sleeve, that is, cover the opening of the sleeve, and further cover the opening of the cup body 5, the fixing base 6 can tightly cover the cup body 5, and after the fixing base 6 completely covers the cup body 5 and it becomes a whole, which is transported, carried, used, stored or discarded as a whole.

The shape of the cup body 5 and/or fixing base 6 is not limited and may be circular, elliptical or polyhedron. In a preferred embodiment, both the fixing base 6 and the cup body 5 are both polyhedrons, that is, the fixing base 6 and the cup body 5 may have polygonal cross sections, which may be triangles, quadrangle, pentagons or other polygons, or may be regular polygons or non-regular polygons.

The fixing base 6 and the cup body 5 may be polyhedrons having the same number of faces, or polyhedrons having different numbers of faces. As shown in FIG. 10 and FIG. 11, in the illustrated embodiment, the cup body 5 is a regular pentahedron, that is, the cup body 5 has a regular pentagon cross section. The shape and side length of the cross section of the inner cover 25 of the sleeve 16 are the same as the cross-sectional shape and the side length of the cup body 5, with a regular pentagon shape. Therefore, the inner cover 25 can tightly cover the opening of the cup body 5, and each side of the inner cover does not extend beyond the sidewall of the cup body 5, so that the cup body 5 can be placed horizontally and stably on the side.

In the illustrated embodiment, the cup body 5 is made of a transparent material, to facilitate the observation of test results.

In some preferred embodiments, one or more detecting elements 3 can be provided in the polyhedral cup body 5, so that different analytes in the sample can be detected simultaneously. In some preferred embodiments, the detecting element 3 is disposed on the inner wall of any of the sidewalls of the polyhedral cup body, or any of the multiple sidewall inner walls, and any of the sidewall inner walls of the cup body 5 can be used for placing the detecting element. In some preferred embodiments, the detecting element 3 is disposed in a space formed by a region between the cup body of the sample receiving cup and the sleeve.

Figure 21:
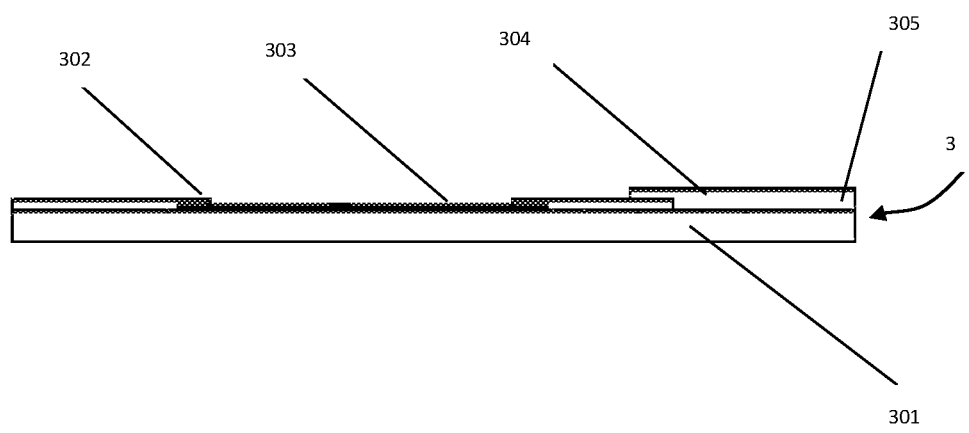
FIG. 21 is a schematic view of a detecting element.

The "detecting element" may be any test apparatus that provides a test result. In some embodiments, the detecting element 3 is a test strip. In a specific embodiment, as shown in FIG. 21, the test strip includes a back side 301, and the front side of the test strip includes a plurality of areas, such as a sample loading area 302, a labeled area 303, a detecting area 304, and a water absorption area 305. The sample loading area 302 includes a sample receiving pad, the labeled area 303 includes a labeling pad, and the water absorption area 305 may include an absorbent pad, wherein the labeling pad has a reagent labeled with a label, such as a gold pad containing a colloidal gold-labeled antibody. The detecting area contains necessary chemicals that can detect the presence or absence of the analyte, for example, immunological reagents or enzyme chemistry reagents. Of course, a control area may be included in downstream of the detecting area. Generally the test strip has a dry chemical reagent component, for example, a fixed antibody or other reagent. When a liquid sample is encountered, the liquid flows along the detecting element with capillary action. With the flow, the dry reagent component is dissolved in the liquid, thus reacting with the colloidal gold-labeled antibody in the next area to perform necessary detection. Liquid flow is primarily carried out by capillary action.

In some preferred embodiments, the apparatus further comprises a placement portion 22 for accommodating a detecting element, the placement portion 22 being disposed in a space formed by an area between the cup body 5 of the sample receiving cup and the sleeve 16. In some preferred embodiments, the placement portion 22 may employ a detection plate. In some preferred embodiments, the placement portion 22 has a slot 28, and the detecting element 3 is disposed in the slot 28 of the placement portion 22. In some preferred embodiments, one or more slots 28 may be disposed on one placement portion 22. In some preferred embodiments, the placement portion 22 may be fixedly connected or may be detachably connected to the cup body 5. In some preferred embodiments, the placement portion 22 is detachably connected to the cup body 5. In some preferred embodiments, the shape of the placement portion 22 is mutually adapted to the shape of the cup body, for example, the cup body is elliptical, then the shape of the placement portion 22 is also elliptical, and the cup body 5 is rectangular, and the shape of the placement portion 22 is also rectangle, such that the outer surface of the placement portion 22 is in contact with the inner surface of the cup body, allowing the inner surface of the cup body to cover the slot 28 of the placement portion. Of course, it is also possible to prevent the outer surface of the placement portion from forming a close fit with the inner surface of the cup body. The placement portion can be fixed in the cup body by bonding or snapping or other detachable means.

In some embodiments, as shown in FIG. 11, in the illustrated embodiment, the cup body 5 is a regular pentahedron, and any one or more sidewalls of the cup body may be provided with a placement portion 22. In some preferred embodiments, as shown in FIG. 11, in the illustrated embodiment, the cup body 5 is a regular pentahedron, and the placement portion 22 is correspondingly disposed on each sidewall of the cup body. In this embodiment, five placement portions 22 which are independent of each other in a rectangular plate-like structure are respectively disposed on the five sidewalls of the cup body. In some preferred embodiments, as shown in FIGS. 11 and 14, the placement portion 22 is an integrally formed regular pentahedron structure, and the placement portion is slightly smaller in size than the cup body, so that the placement portion 22 can be inserted and fixed in the cup body 5.

Figure 14:
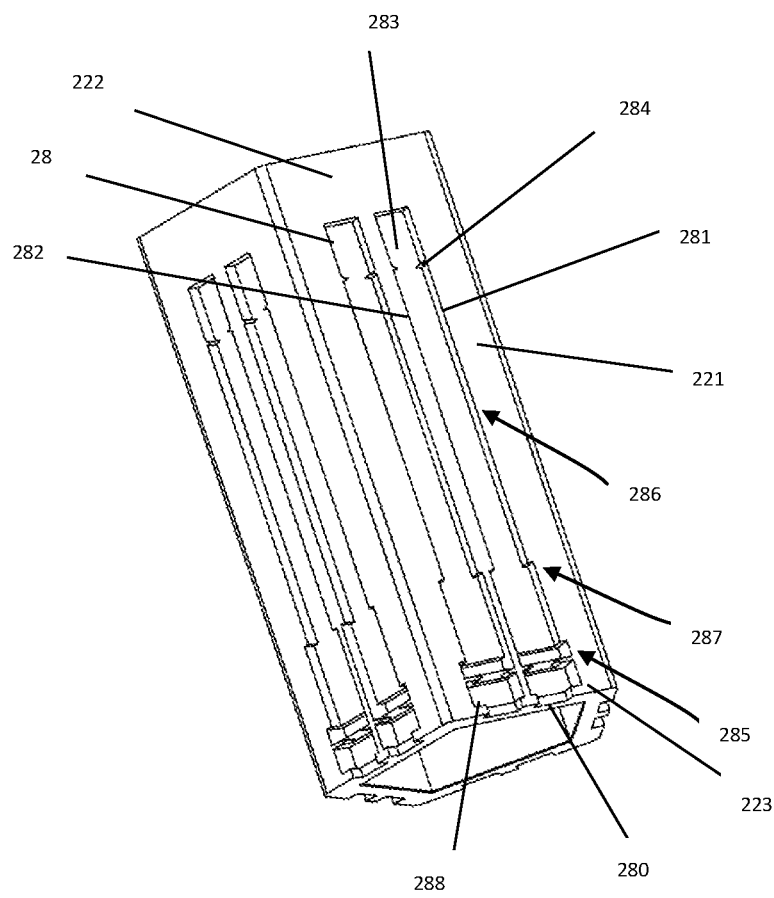
FIG. 14 is a schematic structural view of a placement portion of an apparatus according to another embodiment of the present invention.

As shown in FIG. 14, the placement portion of the present invention comprises a base layer 221, which includes one or more slots 28. The base layer 221 has a certain thickness, and a groove of a certain depth can be formed on the base layer 221 to form a slot 28 for placing a detecting element, and then the detecting element is placed in the slot 28. The width of the slot 28 is equivalent to that of the detecting element 3, or may be greater than the width of the detecting element 3. The depth of the slot 28 is equivalent to the thickness of the detecting element 3, or may be greater than the thickness of the detecting element 3, the length of the slot 28 is equivalent to the length of the detecting element 3, or slightly shorter than the length of the detecting element 3. Generally, in order to save cost and achieve miniaturization of detection apparatus, the width of the slot 28 is slightly larger than the width of the detecting element 3, and the depth of the slot 28 is slightly larger than the thickness of the detecting element 3, and sometimes the width of the slot 28 is equal to or slightly smaller than the width of the detecting element 3, and the depth of slot 28 is slightly less than or equal to the thickness of detecting element 3.

In some preferred embodiments, one end of the slot near the base layer 222 is sealed and one end near the base layer 223 has an opening 280, thereby forming a slot that is sealed at one end and opened at one end. In a preferred embodiment, the length of the slot 28 is slightly shorter than the length of the detecting element, such that the end of detecting element having the water absorption area 305 is located at the upper portion of the slot 28 (on the sealed end of the slot) and the area of the detecting element 3 used for applying samples such as the sample loading area 302 is located near the slot opening 280, or part of the sample loading area 302 of the detecting element is exposed through the opening 280.

As shown from FIG. 14, the slot 28 is formed by a bottom plate 283 and the corresponding left and right sidewalls 281, 282 having a closed end and opening 280. In fact, the base layer 221 of the placement portion 22 has two sides: one side used to open the slot (which may be referred to as the front side of the base layer) and one side as the slot bottom plate 283 (which may be referred to as the back side of the base layer). The thickness of the slot, for example, the thickness of mark 220, may be from 1 mm to 8 mm, such as 1 mm, 2 mm, 4 mm, 5 mm or 8 mm, etc., and may be selected arbitrarily according to different needs.

The base layer 221 of the present invention may be a rigid base layer such as plastic, aluminum alloy, etc. The method of forming a slot on the base layer 221 may be done by one-time injection molding model, or by laser etching. A rigid base layer may be constructed of, for example, a "thermoplastic" material. The "thermoplastic" herein refers to a hot-melt plastic polymer that becomes fluid when heated and solidify into a glass substance when cooled sufficiently. The thermoplasticity may be a polymer of a high molecular weight, and may also include additional constituents such as laser sensitive materials. Some examples of thermoplastic materials may be acrylonitrile butadiene styrene polymer (ABS), acrylic acid polymer (PMMA), celluloid, cellulose acetate or cellulose acetate, cycloaliphatic copolymer (COC), ethylene-vinyl acetate (EVA), ethylene-vinyl alcohol (EVOH), fluoroplastic (PTFE), ionomer or ionomer, acrylic/PVC, liquid crystal polymer (LCP), polyethylene, polyacrylonitrile (PAN or acrylonitrile), polyamide (PA), polyamide-imide (PAI), polyaryletherketone (PAEK or ketone), polybutadiene (PBD), polyethylene terephthalate (PBT), polycaprolactone (PCL), polychlorotrifluoroethylene (PCTFE), polyethylene terephthalate (PET), ethylene terephthalate (PCT), polycarbonate (PC), polyhydroxyl fatty acids (PHAs), polyketones (PK), polyesters, polyethylene (PE), polyetheretherketone (PEEK), polyetherketoneketone (PEKK), polyetherimide (PEI), polyethersulfone (PES), polyethylene chloride (PEC), Polyimide (PI), Polylactic Acid (PLA), Polymethylpentene (PMP), Oxidized Polyphenyl (PPO), Polyphenylene Sulfide (PPS), Poly(orthophenylene) Formamide (PPA), polypropylene (PP), polystyrene (PS), polysulfone (PSU), polyparaphenylene acid propylene glycol ester (PTT), polyurethane (PU), polyvinyl acetate (PVA), polyvinyl chloride (PVC), polyvinylidene chloride (PVDC) and polystyrene-acrylonitrile (SAN), etc.

In some preferred embodiments, as shown in FIG. 14, a fixed structure for fixing the detecting element is provided at one end of the slot 28 near the closed end, for example, a pair of protruding tenon structures 284 is respectively disposed on the opposite sidewalls 281 and 282 that constitute the slot. The tenon structure 284 of the protrusion can be placed on the side of the detecting element 3 to clamp and fix the detecting element 3 in the slot 28. The shape of the tenon structure 284 is not limited as long as it can fix the detecting element, for example, a triangle, a circle or an ellipse, or a combination of any shapes. The detecting element 3, for example the test strip, has elasticity, after the test strip is placed into the slot 28, the tenon structure 284 can withstand the sidewall of the test strip, thereby fixing the test strip in the slot 28. The number of tenon structures 284 can be two, three, four or more. The tenon structure 284 can be evenly distributed or unevenly distributed around the left and right sidewalls of the slot. In one embodiment, two tenon structures 284 are disposed on one end of the slot near the base layer 222, and the two tenon structures 284 are symmetrically arranged, that is, the symmetrical left and right sidewalls in the slot 28 have a tenon structure 284 respectively, which can keep the testing elements from falling off from the slot.

In some preferred embodiments, the slot 28 includes a structure for reducing, limiting or eliminating capillary flow. The structure is located on the slot, especially, on the bottom plate of the slot or the sidewall of the slot, thereby allowing liquid to flow on the detecting element without flowing along the gap formed between the detecting element and the slot to the greatest extent. The gap is a capillary gap. The term "reducing" is to allow part of liquid not to flow through the capillary gap. The term "limiting" is to allow liquid not to flow through the capillary gap to the greatest extent, and the term "eliminating" means that none of liquid flows through the capillary gap, for example, 100% blocking, 95% blocking, 90% blocking, and 89% blocking.

Usually, the liquid can only flow from upstream to downstream along the test strip based on capillary action on the test strip. If additional liquid enters the slot, it will cause the liquid sample to flow earlier than the capillary action based on the test strip itself. The liquid that reaches the downstream area earlier dissolves or wets the test strip, causing abnormal detection, which may produce a "flooding" phenomenon. The liquid that enters the slot to cause flooding is called abnormal liquid sample or additional liquid sample, because the abnormal capillary flow is only the flow of the liquid samples, and the normal liquid which relies on the capillary action of the test strip itself can dissolve the reagents processed on the test strip, for example, the labeled reagent, the reagent for processing liquid samples, etc., which will not affect the detection accuracy and sensitivity.

Generally, by minimizing the abnormal liquid that enters the slot and allowing more normal liquid to be absorbed through the test strip itself, the test results will be more accurate. On the contrary, if the flow of abnormal liquid is not controlled in the slot, the capillary action on the test strip will be affected, which ultimately leads to inaccurate detection results. In severe cases, the test strip will not work properly.

The upstream or downstream as used herein is divided according to the direction of liquid flow, generally liquid flows from upstream to downstream. The downstream receives liquid from the upstream and the liquid can also flow along the upstream to the downstream. Here, it is generally divided according to the direction of liquid flow. For example, on some materials that promote the flow of liquid by the capillary force, the liquid can flow in the opposite direction of gravity. At this time, the upstream and downstream are divided according to the direction of the liquid flow. In the present invention, the liquid flows from the sample loading area 302 of the test strip to the labeled area 303 and the detecting area 304. When the sample loading area 302 is the upstream area, the downstream of the sample loading area 302 may be the labeled area 303, the detecting area 304, and the water absorption area 305 sequentially.

For the placement portion 22 of the present invention, there are mainly two places where a capillary gap is generated; for the first one, a capillary gap may be generated between the test strip and the bottom plate 283 of the slot, to generate capillary flow. When the test strip is placed in the slot 28, generally the back side 301 of the test strip is directly in contact with the bottom plate 283 of the slot, to form a gap structure between the bottom plate 283 of the slot and the test strip, for example, a capillary gap structure. When there are many samples and the placement portion 22 is inserted (immersed) into the liquid samples, part of the liquid sample may flow upward through the capillary gap formed between the bottom plate 283 of the slot and the test strip back side 301, thereby generating a flooding. For the second one, a capillary gap may be generated in the distance between the side of the test strip and the surface of the sidewalls 281, 282, causing capillary flow. These capillary flows are undesirable. In some preferred embodiments, the capillary flow is a capillary gap formed between the detecting element and the slot sidewall, or a capillary gap formed between the detecting element and the bottom plate of the slot.

Figure 15:
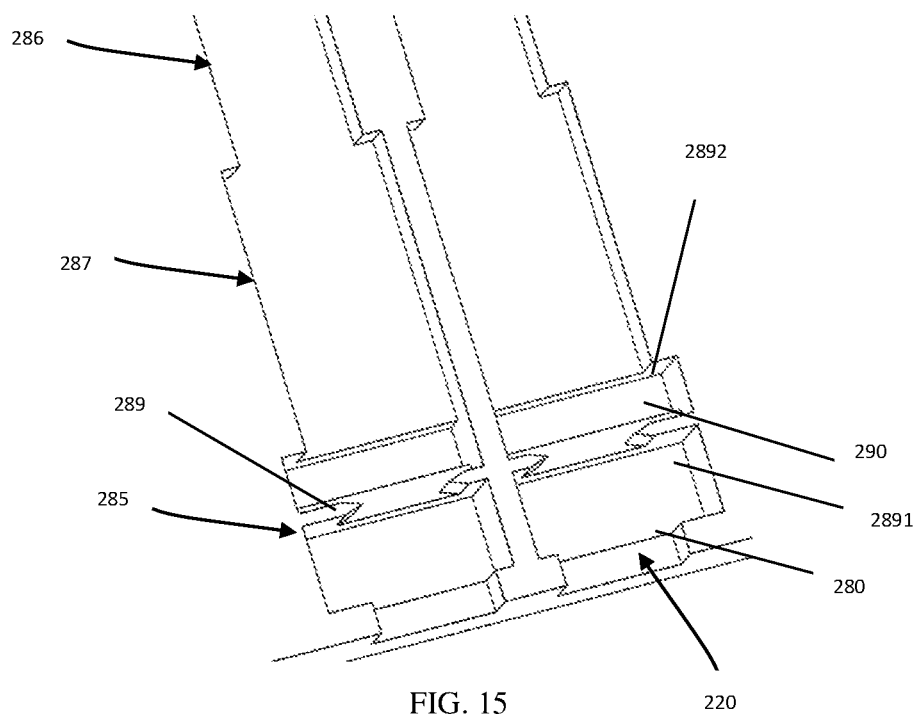
FIG. 15 is a partially enlarged schematic view of FIG. 14.

In some preferred embodiments, the slot 28 includes a structure for reducing, limiting or eliminating capillary flow, that is, an anti-flooding structure, which can reduce or avoid capillary flow of liquid outside the test strip, i.e. the structure can allow liquid to flow on the testing element through the capillary force of the test strip itself to the greatest extent, to reduce the flow of the capillary gap formed between the test strip and the slot. In some preferred embodiments, the anti-flooding structure includes a recess 288 disposed on the slot bottom plate 283, as shown in FIGS. 14 and 15, the slot 28 forms a chamber body 289 at the recess 288 for containing excess samples, that is, it is equivalent that there is a region that is hollowed on the bottom plate 283 of the slot, to form a chamber body 289 for accommodating excess samples, that is, the depth of the slot having the recess is different from the depth of the slot having no recess. In some preferred embodiments, the chamber body 289 is located at the opening 280 of the slot. In the case of a large number of liquid samples, the chamber body 289 can store or absorb or retain excess liquid when entering the slot 28 from the opening 280, such that the excess liquid cannot or substantially cannot move along the bottom plate 283 of the slot toward the downstream area, thereby avoiding capillary flow between the slot bottom plate 283 and the test strip.

The chamber formed by these recess structures can fill the bottom plate 283 of the entire slot, or can be limited to some locations. Preferably, the chamber formed by these recess structures is located at a position of the slot. In some aspects, the chamber formed by these recess structures is located at the sample loading area 302 of the test strip. In some embodiments, the chamber formed by these recess structures is located upstream of the labeled area of the test strip, and the "upstream of the labeled area of the test strip" as described herein means that the chamber formed by the recess structure is distributed on the slot bottom plate 283 corresponding to the upstream region of the labeled area of the test strip. In some embodiments, the chamber formed by these recess structures is located between the sample loading area of the test strip and the labeled area. The "located between the sample loading area of the test strip and the labeled area" herein means that the chamber formed by these recess structures is distributed on the slot bottom plate corresponding to the area between the sample loading area of the slot and the test strip. Due to the presence of the chamber on the bottom plate, the liquid enters the chamber, thereby being blocked or reduced here, and liquid samples will not wet the labeled area in advance.

The shape of the chamber body 289 is not limited and may be rectangular, square, circular, elliptical or other suitable shape as long as it can be used to accommodate or retain excess liquid sample. In a preferred embodiment, the shape of the chamber body 289 is a rectangle. In a preferred embodiment, there are one or more chambers. In a preferred embodiment, there are 2 chamber bodies 289 on the slot bottom plate.

In a preferred embodiment, the anti-flooding structure divides the slot 28 into two parts, as shown in FIGS. 14 and 15, the first portion 285 with a recess on the slot bottom plate and the second portion 286 without a recess on the slot bottom plate, wherein the width of the first portion 285 is greater than that of the second portion 286. In this embodiment, the slot for placing the test strip is a rectangle, and the width of the slot is equal or substantially equal to the test strip, wherein the first portion 285 with a recess on the slot bottom plate is located at the opening 280 of the slot, that is, the segment of the slot having the recess from opening to the bottom plate, i.e. the first portion, and the other segment located at downstream of the first portion is the second portion 286. The slot bottom plate of the first portion 285 has a rectangular chamber body 289, and the width of the rectangular chamber body 289 is greater than the width of the second portion of slot, that is, the slot sidewall corresponding to the first portion extends outward such that the width of the portion of the slot is greater than the width of the second portion. In some preferred embodiments, the width of the second portion 286 is equal or substantially equal to the width of the test strip. When the test strip is placed in the slot, since the width of the first portion 285 is larger than the width of the test strip, the side of the test strip is far enough apart from the sidewall of the slot, such that there is no capillary gap between the side of the test strip and the slot sidewall, which blocks the capillary flow of the liquid. In some preferred embodiments, the width of the first portion 285 is 1 to 15 mm wider than the second portion. In some preferred embodiments, on the card slot sidewall with recess, there is a protrusion 290 for holding the test strip. Since the width of the first part of slot having the recess is larger than the width of the test strip, the protrusion 290 is disposed on the sidewall for snapping the test strip in the slot, to prevent the test strip from falling or shaking due to the impact of the liquid, resulting in unstable detection results. In some preferred embodiments, the protrusion 290 is located in the left and right sidewalls corresponding to the slot. In some preferred embodiments, as shown in the figure, there are two chamber bodies 289 formed by recess at the bottom of the slot for accommodating excess liquid, including a first chamber body 2891 and a second chamber body 2892, wherein the first chamber body 2891 is located at slot opening 280, and the second chamber body 2892 is located downstream of the first chamber body 2891. In some preferred embodiments, the first chamber body 2891 has an area larger than the second chamber body 2892 and is capable of storing or absorbing or retaining more liquid. In some preferred embodiments, there is a protrusion 290 facing the slot on the slot sidewall between the first chamber body 2891 and the second chamber body 2892, and the protrusion 290 is a tenon structure, which can clamp or fix the test strip. Since the test strip is elastic, the tenon structure's protrusion 290 can hold the side of the test strip to play a role of fixation. This structure can not only fix the test strip, but also have other functions. This structure can reduce, prevent or limit capillary flow. For example, the structure can be raised from the sidewall, and when the test strip is placed in the slot, the raised tenon squeezes the test strip. Due to the tight pressing contact between the tenon structure and the test strip, the liquid from the upstream of the tenon is blocked at the tenon, thus the liquid cannot continue to flow downstream along the capillary gap, thereby avoiding the liquid passing through the capillary gap to reach the downstream area earlier than the liquid of the test strip. Such a raised tenon structure may be located between the first chamber body 2891 and the second chamber body 2892, or may be located at the junction of the second chamber body 2892 and the second portion of the slot. The structures similar to the tenon may also be some other structures as long as it has one or more functionally similar structures as described above, for example, the tenon structure actually protrudes inwardly from the surface of the slot sidewall, and is higher than the plane of the sidewall, thereby allowing the slot to become narrow at the tenon. The tenon can be symmetrically distributed on the surface of the two sidewalls, and of course, not necessarily symmetrical distribution. As shown in FIG. 15, after the excess liquid enters the slot from opening, the first chamber absorbs the excess liquid, and the liquid is retained in the first chamber, the tenon structure located between the first chamber and the second chamber prevents the liquid from flowing towards downstream. When too much liquid causes the first chamber to be filled, the excess liquid enters the second chamber, and through the cooperation of two chambers, the excess liquid entering the slot is further retained.

In another preferred embodiment, the slot of the second portion 286 further comprises a third portion 287 having a width greater than the portion of the slot, as shown in FIGS. 14 and 15, the downstream portion of the first portion 286 has an area with the width greater than the second portion, and this slot is called third portion 287. The third portion 287 is equivalent to having a recess in the sidewall of the card slot. This recess increases the distance between the side of the test strip and the sidewall of the slot, which is greater than the distance of the capillary action. In some preferred embodiments, the width of the third portion is 1 to 10 mm wider than the second portion. In a preferred embodiment, the third portion 287 has a width smaller than the first portion 285. In a preferred embodiment, the third portion 287 is located between the first portion 285 and the second portion 286. In a preferred embodiment, the third portion 287 is located in the sampling loading area 302 of the test strip, or below the sample loading area 302 of the test strip, or between the sampling loading area 302 and the labeled area 303 of the test strip, or the labeled area of the test strip 303. Such a setting is to prevent the liquid from flowing downstream along the side of the test strip and the capillary gap of the slot sidewall when the first chamber body 2891 and the second chamber body 2892 of the first portion 285 are filled due to excessive samples into the slot.

The slot of the placement portion of the detecting element provided by the present invention has different width settings and has different depth settings. For example, as shown in FIG. 14 and FIG. 15, the width of the first portion 285 of the slot is greater than the width of the second portion 286, the width of the second portion 286 is greater than the width of the third portion 287, and the width of the third portion 287 is equal to the width of the detecting element 3 or Substantially equal, the width from the upstream to the downstream of the slot is gradually reduced. This reduction in width can be a sudden decrease or a gradual decrease by controlling the width upstream of the slot to be larger than the width of the detecting element. It eliminates the capillary gap between the sides of the detecting element and the slot sidewall, thereby reducing the capillary flow of additional liquid between the sides of the detecting element and the slot sidewall. The depth of the first portion of the slot is greater than the depth of the second and third portions, i.e., the height of the different portions of the slot is different, and the bottom portion of the first portion of the slot has a recess, forming a cavity for storing or absorbing additional liquid, additional The liquid can enter the cavity and be retained without being able or substantially unable to move to the downstream region.

In the illustrated embodiment, as shown in FIGS. 16-19, a protrusion structure 4 that protrudes inwardly to the cup body is provided at the bottom of the cup body of the sample receiving cup, making the bottom of the cup body in a concave shape. The protrusion structure 4 causes the sample receiving cup to form a space with respect to the cup body protrusion and a space with respect to the bottom recess, and a first liquid collecting area 51 is formed between the protrusion structure and the cup body sidewall. In some preferred embodiments, the first liquid collecting area 51 is a ring structure surrounding the protrusion structure. In some preferred embodiments, the sample loading area of the detecting element is located in the first liquid collecting area for sucking the samples to perform the detection of analytes.

In some preferred embodiments, the protrusion structure comprises a central top portion 40, and a slope extending from the central top portion to the first liquid collecting area, the liquid samples enter the first liquid collecting area via the surface of the slope. In some preferred embodiments, the protrusion structure 4 is a conical protrusion, that is, the central top portion 40 is a shape protruding inwardly toward the inside of the cup body. In some preferred embodiments, the protrusion structure 4 is a circular truncated cone boss, that is, a central top portion is a plane, the circular truncated cone has a maximum diameter at the bottom of the cup body, the top of the circular truncated cone is below the bottom of the sleeve, and the circular truncated cone and the sidewall of the cup body enclose to form a first liquid collecting area 51 at the bottom. In some preferred embodiments, when the sleeve 16 is nested in the cup body 5, the protrusion structure 4 has the same circular axis as the sleeve 16. In some preferred embodiments, the surface of the protrusion structure 4 acts as a flow-guiding structure to guide liquid to flow from sleeve 16 to the first liquid collecting area 51, that is, samples from the collecting element 15 flow to the protrusion structure 4 via the notch 161 at the bottom of the sleeve, and then flow from the protrusion structure 4 to the first liquid collecting area 51. In the present invention, the samples for detecting the analytes may be blood, urine or saliva, etc., for a liquid having a certain viscosity or poor fluidity, such as saliva, if the liquid samples are directly applied to the sample receiving cup 1 via the notch 161 of the sleeve, samples may enter an area of the first liquid collecting area 51 in a droplet shape, and then flow from the area to other areas of the first liquid collecting area. Due to the poor fluidity, samples cannot be received uniformly in the sample loading area 302 of detecting element 3 located at the first liquid collecting area 51, so that there is time difference for receiving samples for different detecting elements, which may cause detection errors; For liquids with good fluidity such as urine, if the samples are directly applied to the sample receiving cup 1 via the notch 161 of the sleeve, a large amount of samples may enter an area of the first liquid collecting area 51 in a droplet form. At this time, they may cause impact or washing on the detecting element that contact the samples at the first time, resulting in a detection error. As described above, the protrusion structure 4 of the present invention is used as a flow-guiding structure for guiding the liquid samples into the first liquid collecting area 51, the term "guiding" herein means that the protrusion structure 4 can have the function of flow guiding or slow flowing, allowing liquid that enters the sample receiving cup to be guided through some physical structure on the surface of the protrusion structure 4 to enter the first liquid collecting area 51 in a desired manner. The term "flow guiding" herein means that the liquid samples from the collecting element 15 can be uniformly guided to the specific target area by a physical structure, to minimize the liquid samples to flow to the undesired area, or unevenly reach a specific target area. The term "slow flow" as used herein means that the liquid with high fluidity reaches a specific target area uniformly and gently under the guidance of a physical structure, to prevent a large amount of liquid from rapidly impacting the detecting element. In the present invention, the promotion structure is used to guide the liquid to uniformly enter the first liquid collecting area 51, and play a slow-flowing effect on liquid having a strong fluidity, thereby avoiding the occurrence of the stripping phenomenon. As shown in FIG. 11, in the present invention, the cup body 5 of the sample receiving cup 1 is a regular pentagon, and a plurality of detecting elements 3 are evenly distributed on five sidewalls of the regular pentagon cup body. Samples that are desired to enter the first liquid collecting area 51 can reach the sample loading area 302 of each test element 3 uniformly and even simultaneously, to ensure that each test element 3 can simultaneously contact substantially the same number of samples, thereby reducing detection errors and improving detection sensitivity.

Figure 17:
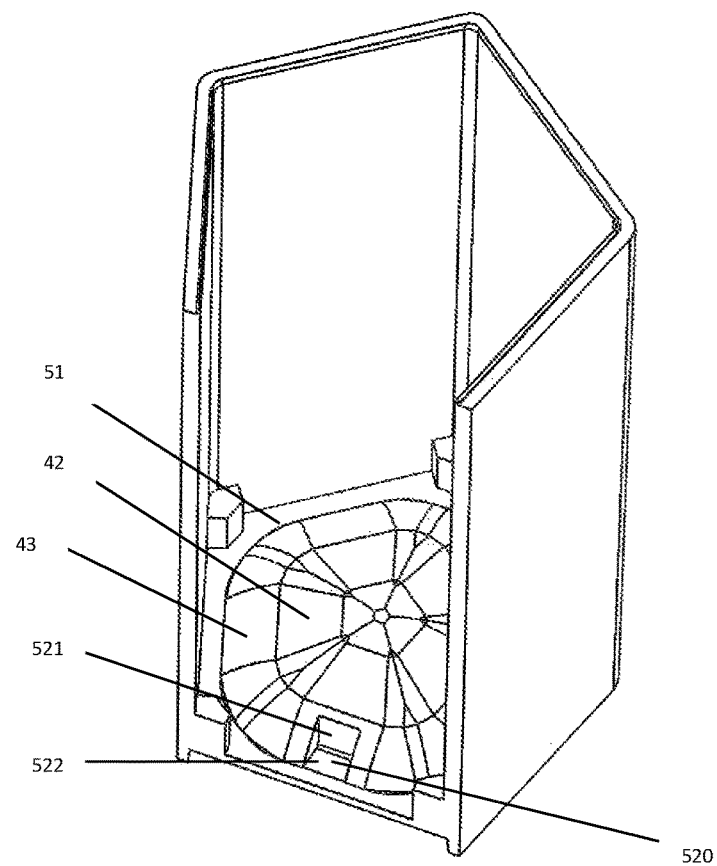
FIG. 17 is a cross-sectional view of a sample receiving cup of the apparatus according to another embodiment of the present invention.
Figure 18:
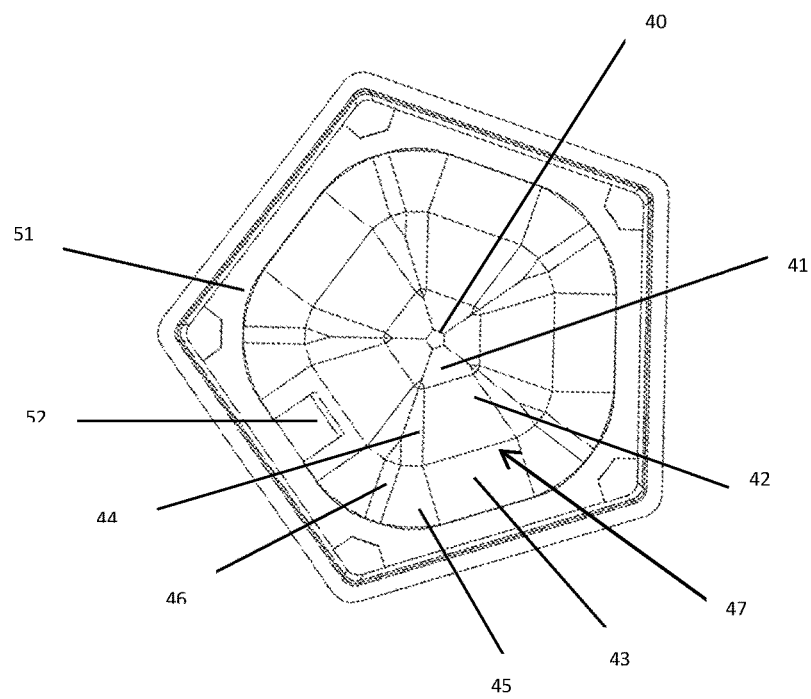
FIG. 18 is a top view of the bottom of a sample receiving cup of the apparatus according to another embodiment of the present invention.

In some preferred embodiments, the slope surface of the protrusion structure 4 is composed of a plurality of arc-shaped curved surfaces which are curved inwardly, and each curved surface constituting the protrusion structure 4 serves as a flow guiding element that constitutes the flow-guiding structure for guiding the liquid to enter the first liquid collecting area 51. In some preferred embodiments, as shown in FIGS. 17 and 18, the cup body 5 of the sample receiving cup 1 is a regular pentahedron, the detecting element 3 is uniformly disposed on the five sidewalls of the cup body 5, and the protrusion structure 4 at the bottom of the cup body correspondingly consists of five repeating units that correspond to the five sidewalls of the cup body. In some preferred embodiments, the central top portion 40 of the protrusion structure is a plane such that the protrusion structure has a circular truncated cone shape. In some preferred embodiments, the protrusion structure includes a first curved surface 41 connected to the central top portion 40, a second curved surface 42 connected to the first curved surface 41, and a third curved surface 43 connected to the second curved surface 42, the end of the third curved surface 43 is connected to the first liquid collecting area 51. The first curved surface 41, the second curved surface 42 or the third curved surface 43 is an area for receiving a liquid sample, thereby forming an area similar to an equilateral triangle or an isosceles triangle on the protrusion structure. The liquid from the collecting element 15 flows into the first liquid collecting area 51 through the area. In some preferred embodiments, for the protrusion structure, the first curved surface 41 serves as a central top portion of the protrusion structure, so that the protrusion structure 4 has a conical shape. In some preferred embodiments, the protrusion structure 4 does not have a first curved surface 41, and the central top portion 40 connects the second curved surface 42, and the third curved surface 43 connects the second curved surface 42 to form an area in which the liquid flows. The shape of the central top portion 40 is not limited and may be a circular, elliptical, regular or irregular polygon such as a triangle, a square, a pentagon, etc. In some preferred embodiments, as shown in FIGS. 17 and 18, the central top portion 40 is a plane having a regular pentagon shape, and the five sides of the central top portion 40 correspond to the five sidewalls of the cup body, respectively.

Figure 19:
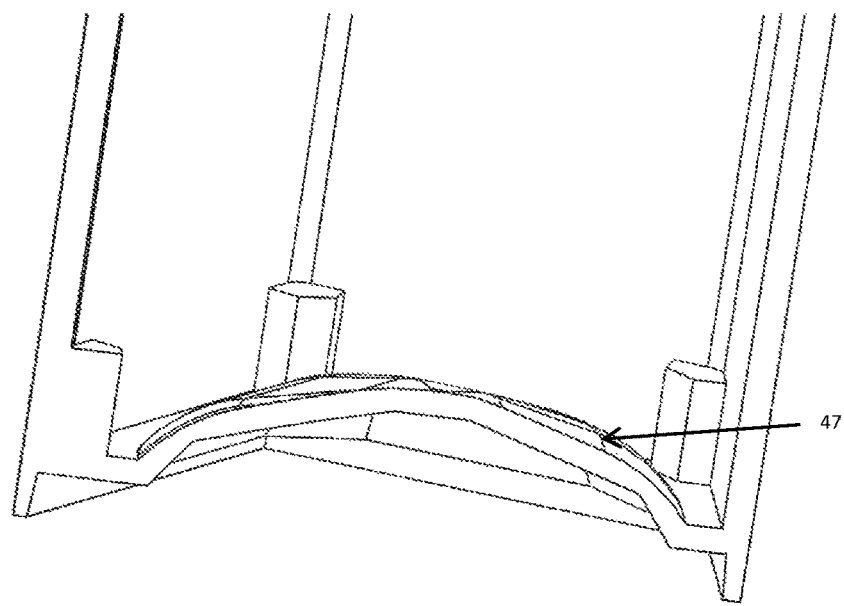
FIG. 19 is a cross-sectional view of the bottom of a sample receiving cup of the apparatus according to another embodiment of the present invention.

In some preferred embodiments, as shown in FIG. 19, the first curved surface 41, the second curved surface 42 and the third curved surface 43 that constitute the protrusion structure 4 have different radians, that is, the first curved surface 41, second curved surface 42 and third curved surface 43 have a different degree of curvature, so that the protrusion structure 4 can play a role of flow-guiding or flow-slowing.

In some preferred embodiments, the notch 161 at the bottom of the sleeve is disposed above the first curved surface 41 or the second curved surface 42 or the third curved surface 43, or between the first curved surface 41 and the second curved surface 42, or between the second curved surface 42 and the third curved surface 43, that is, when the sleeve is fixed in the sample receiving cup, the notch 161 at the bottom of the sleeve is directly opposite to any curved surface or between any two curved surfaces, and the liquid from the collecting element 15 passes through the notch 161 of the sleeve to drip on any one curved surface or between any two curved surfaces of the protrusion structure, and the curved surface that first contacts the sample is used as the first receiving area of the liquid samples, which is related to the cross-sectional area of the bottom of the sleeve, the position of the sleeve notch and the area of the curved surface.

In some preferred embodiments, the notch 161 at the bottom of the sleeve is disposed above the second curved surface 42, which is the first receiving area of the liquid sample. As shown in FIG. 19, the second curved surface 42 has a lower radian relative to the first curved surface 41 and the third curved surface 43, and the second curved surface 42 is close to a slope. When liquid drips on the second curved surface 42, the liquid with poor fluidity, for example saliva, can easily flow toward the bottom circle of the protrusion structure 4. In some preferred embodiments, the height of the first curved surface 41 is higher than the second curved surface 42, that is, the surface of the first curved surface 41 protrudes more toward the cup body than the surface of the second curved surface 42, which is higher than the second curved surface 42 by 0.1~0.5 mm. In some preferred embodiments, one edge is protruded at the intersection of two adjacent first curved surfaces 41. In some preferred embodiments, the third curved surface 43 is a smooth curved surface, and there is a smooth transition between the second curved surface 42 and the third curved surface 43, and the curvature of the third curved surface 43 is greater than that of the second curved surface 42. The liquid from the second curved surface 42 can enter the first liquid collecting area 51 along the third curved surface 43. In some preferred embodiments, a smooth boss 47 is provided between the second curved surface 42 and the third curved surface 43. In some preferred embodiments, the smooth boss is located on the third curved surface 43. In some preferred embodiments, the smooth boss 47 is located at the other end of the third curved surface 43, i.e. a smooth boss 47 is provided at the end of the third curved surface 43 for connection with the second curved surface 42, that is, there is a smooth boss 47 at the intersection of the second curved surface 42 and the third curved surface 43, and the smooth boss 47 is slightly higher than the second curved surface 42 by 0.1 mm, 0.2 mm, 0.3 mm, 0.4 mm, 0.5 mm, etc. The boss can block the liquid from the second curved surface 42, but the blocking effect is insufficient to block liquid from flowing through its surface, i.e. the boss does not block or substantially block the flow of liquid through its surface. The location of the smooth boss is shown by the arrows in FIGS. 18 and 19. The smooth boss 47 has two functions: firstly, when the liquid drips onto the second curved surface 42, the droplets will spread to some extent on the second curved surface 42, when encountering the smooth boss 47, the boss has a blocking effect, so that the liquid is further spread, thereby uniformly entering the first liquid collecting area along the third curved surface 43, or the boss can collect a plurality of droplets and then spread them, to allow a sufficient amount of liquid to uniformly and dispersedly enter the first liquid collecting area; secondly, for a large number of samples that are rapidly dripping, especially for liquids with high fluidity, the boss has a blocking effect, so that the liquid enters the first liquid collecting area 51 along the third curved surface 43 at a relatively slow speed, to avoid shock on the detecting element. In some preferred embodiments, the end of the third curved surface 43 corresponds to the sampling loading area 302 of the detecting element 3, that is, the sampling loading area 302 of the detecting element is located in the space between the end of the third curved surface and the cup body sidewall. In some preferred embodiments, the placement portion 22 accommodating the detecting element 3 is located in a space between the end of the third curved surface and the cup body sidewall, wherein the placement portion 22 has a plurality of slots 28, a sampling loading area 302 or a portion of the detecting element is exposed by the opening 280 of the slot, and the length of the end of the third curved surface is equal to or slightly larger than the distance between the openings of a plurality of slots on the placement portion. The distance herein refers to the distance between the opening of the first slot and the opening of the last slot. In a preferred embodiment, the placement portion has 2 slots, and the length of the end of the third curved surface is equal to the distance between the openings of two slots on the placement portion.

In some preferred embodiments, as shown in FIGS. 17 and 18, the detecting element 3 is located on the sidewall of the pentagon cup body. For a liquid having poor fluidity such as saliva, since it is not easily uniformly dispersed, when it passes through the surface of the protrusion structure 4 to flow to the first liquid collecting area 51, it is desirable that the liquid flows as much as possible to the position of the sampling loading area of the detecting element, and does not flow to the area without the detecting element, for example, the five apex angles of the pentagon cup body, that is, it is desirable to have liquids entering a particular target area while reducing the flow to non-target areas. In the preferred embodiment, as shown in the figure, a structure for restricting liquid flow to a non-target area, for example, to a vertical angle of a pentagon cup body, is provided on the protrusion structure 3. Specifically, slightly convex curved surfaces are provided on both sides of the first curved surface 41, the second curved surface 42, and the third curved surface 43, thereby restricting the flow of the liquid within a specific range. In some preferred embodiments, the liquid restricting structure limits the flow of liquid on the surface of the protrusion structure to an area between the first curved surface 41, the second curved surface 42 and the third curved surface 43. In some preferred embodiments, the flow of liquid on the surface of the protrusion structure is the area between the second curved surface 42 and the third curved surface 43, that is, the liquid from the collecting element flows through the second curved surface 42 and the third curved surface 43 to the first liquid collecting area 51.

In some embodiments, as shown in the figure, a fourth curved surface 44 is disposed on the left and right sides of the second curved surface 42. The height of the fourth curved surface 44 is higher than that of the second curved surface 42, that is, the surface of the fourth curved surface is more protruding inwardly to the cup body relative to the surface of the second curved surface, such that liquid from the second curved surface 42 cannot flow onto the fourth curved surface 44. In some preferred embodiments, the fourth curved surface 44 is higher than the second curved surface 42 by 0.1 mm, 0.2 mm, 0.3 mm, 0.4 mm, 0.5 mm, etc. In some preferred embodiments, the convex direction of the fourth curved surface 44 faces towards the second curved surface 42. In some preferred embodiments, the fourth curved surface 44 intersects the end of the central top portion 41. In some preferred embodiments, an edge is protruded at the intersection of two adjacent four curved surfaces 44.

In some embodiments, as shown in the figure, a fifth curved surface 45 is disposed on the left and right sides of the third curved surface 43. The height of the fifth curved surface 45 is higher than that of the third curved surface 43, that is, the surface of the fifth curved surface 45 is more protruding inwardly to the cup body relative to the surface of the third curved surface 43, such that liquid from the second curved surface 42 and/or the third curved surface 43 cannot flow onto the fifth curved surface 45. In some preferred embodiments, the fifth curved surface 45 is higher than the third curved surface 43 by 0.1 mm, 0.2 mm, 0.3 mm, 0.4 mm, 0.5 mm, etc. In some preferred embodiments, the convex direction of fifth curved surface 45 faces towards the third curved surface 43. In some preferred embodiments, a sixth curved surface 46 is provided between two adjacent fifth curved surfaces 45.

In some preferred embodiments, the protruding height of the smooth bosses 47 on the fourth curved surface 44, the fifth curved surface 45, the central top portion 41 and the third curved surface is equal.

In some preferred embodiments, as shown in the figure, the protrusion structure 4 at the bottom of the cup body of the present invention is composed of five repeating units, each of which comprises a first curved surface 41, a second curved surface 42, a third curved surface 43, a fourth curved surface 44 disposed on the left and right sides of the second curved surface 42 and a fifth curved surface 45 disposed on the left and right sides of the third curved surface 43. In the present embodiment, the second curved surface 42 is the first receiving area of the liquid samples, and the liquid from the collecting element uniformly flows to the first liquid collecting area 51 after dispersed by the second curved surface 42 and the third curved surface 43. The number of repeating units constituting the protrusion structure is not limited, and it is related to the cup body shape of the sample receiving cup and the position of the detecting element in the cup body, for example, for a square cup body, the number of repeating units may be four, and for a triangular chamber, the number of repeating units can be three.

Figure 16:
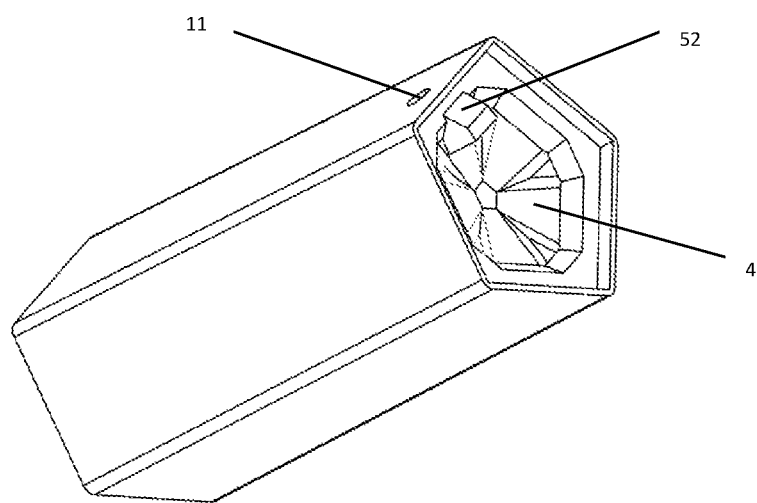
FIG. 16 is a bottom view of a sample receiving cup of the apparatus according to another embodiment of the present invention.

In some preferred embodiments, a second liquid collecting area 52 is further disposed on the bottom of the cup body. The second liquid collecting area 52 is used to collect liquid samples for second detection; and when there are too many liquid samples entering the cup body, the second liquid collecting area 52 is used to store excess liquid. In some preferred embodiments, the second liquid collecting area 52 or a part of the second liquid collecting area 52 is disposed on the protrusion structure 4. In some preferred embodiments, the second liquid collecting area 52 or a part of the second liquid collecting area 52 is disposed on a slope that constitutes the protrusion structure. In some preferred embodiments, the second liquid collecting area 52 is a chamber that is disposed on the protrusion structure 4 and is convex with respect to the bottom of the cup body. As shown in FIG. 16, the convex chamber is formed by protruding the bottom of part of the cup body outwardly from the cup body, which is located in the space of the sample receiving cup relative to the bottom recess. In some preferred embodiments, the opening 520 of the second liquid collecting area is located on a slope of the protrusion structure 4. In some preferred embodiments, the opening 520 of the second liquid collecting area is located on the third curved surface 43 of the protrusion structure 4, that is, the third curved surface 43 has a notch, and the bottom of the cup body at the notch protrudes outwardly to form a chamber for receiving liquid. The shape of the opening 520 is not limited and may be a circle, an ellipse, a polygon, such as a triangle, a quadrangle, etc. In some preferred embodiments, as shown in FIG. 17, the opening 520 of the second liquid collecting area has a square shape. In some preferred embodiments, the upper portion of the opening 520 of the second liquid collecting area is located on the smooth boss 47 of the third curved surface, and the lower portion of the opening is located at the end of the third curved surface connected to the first liquid collecting area. In some preferred embodiments, the upper portion of the opening 520 of the second liquid collecting area is located at the position of ½ of the smooth boss of the third curved surface, and the lower portion of the opening is located at the end of the third curved surface connected to the first liquid collecting area.

The shape of the convex chamber of the second liquid collecting area 52 is not limited and may be a spherical, cylindrical chamber, a cube, a cuboid, and other irregular shapes. In some preferred embodiments, as shown in FIG. 17, the convex chamber comprises a straight surface 521 that is perpendicular to the cross section of the cup body, the straight surface 521 being longitudinally parallel to the sidewall of the cup body. The convex chamber further comprises a slope 522 that is in communication with the first liquid collecting area 51. As shown in FIG. 17, when the liquid from the second curved surface flows through the opening of the convex chamber, due to the presence of the smooth boss 47 and the straight surface 521, surface tension may exist at the opening of the convex chamber, and the liquid will not enter the second liquid collecting area at the first time, but firstly enter the first liquid collecting area. The liquid from the second curved surface herein refers to the liquid dripped from the notch 161 of the sleeve onto the second curved surface.

In some preferred embodiments, the second liquid collecting area 52 is in fluidic communication with the first liquid collecting area 51. "Fluidic communication" means that the fluid can flow from one place to another, and may pass through some physical structures may have a guiding role in the process of flowing. The wording "pass through some physical structures" herein means that the liquid passes through the surface of these physical structures or the internal space of these structures to flow to another place passively or actively. The "passively" is generally caused by external forces. In some preferred embodiments, the opening 520 of the second liquid collecting area 52 is in communication with the first liquid collecting area 51, and the liquid from the first liquid collecting area 51 can enter the second liquid collecting area 52 through the opening 520. In some preferred embodiments, the slope 522, as a convex chamber of the second liquid collecting area 52, enables the liquid in the first liquid collecting area 51 to smoothly enter the convex chamber smoothly, such that samples are collected in the second liquid collecting area 52. In some preferred embodiments, the cup body 5 is molded by one-time injection mold.

In some preferred embodiments, as shown in FIG. 11 and FIG. 16, the apparatus comprises a secondary sampling port 11, which is disposed on a sidewall of the cup body 5 so that operators can take out samples from the cup body 5 for second confirmatory detection. At this time, the sample receiving cup 1 can be conveniently kept in the closed state and still allows the liquid samples to be taken out. In a preferred embodiment, the apparatus is in a sealed state before the secondary sampling port 11 is used. In some preferred embodiments, the secondary sampling port 11 is sealed by a sealing element. In a preferred embodiment, the sealing element for sealing the secondary sampling port 11 is a fragile element. When sampling from the secondary sampling port 11 is required, the fragile element can be lightly pierced to expose the secondary sampling port 11, that is, the secondary sampling port is a structure that is easy to pierce. In the present invention, the fragile element is an easily broken element or an easily pierced element, which may be a film, a glass, a sticker, a film plastic, a plastic sheet, etc. Correspondingly, a rigid or sharp piercing element can be used to puncture, break or pierce the fragile element, thereby exposing the secondary sampling port 11, for example, the piercing element can be a straw or a gun for sampling. Such setting is easy to implement in the art, and specifically there are many ways. For example, when manufacturing the detection apparatus of the present invention, a small hole may be opened at a corresponding position of the cup body sidewall, and then a small film or a self-adhesive or a plastic sheet is covered on the small hole to seal the hole, or during one-time injection molding, the thickness of the cup body sealing the secondary sampling port is smaller than the thickness of the cup body sidewall. In other preferred embodiments, the sealing element for sealing the secondary sampling port 11 is a structure detachably separable from the secondary sampling port 11 such as a plug, a card, etc., and can be removed from the sealed secondary sampling port 11 to open the secondary sampling port 11, or can be inserted into the secondary sampling port 11 for sealing.

In some preferred embodiments, the secondary sampling port 11 is disposed on a cup body sidewall opposite to the second liquid collecting area 52. In some preferred embodiments, the second sampling port 11 is in communication with the second liquid collecting area 52. The term "communication" as used herein means that the samples collected in the second liquid collecting area 52 can be taken out via the secondary sampling port 11 for second detection. In the present invention, the secondary sampling port 11 cooperates with the opening 520 of the second liquid collecting area 52 to facilitate the sampler such as a gun, a straw, etc. to easily enter the second liquid collecting area 52. The detection apparatus needs not to be tilted when taking samples, making the operations more conveniently and quickly. In addition, a solvent or other desired substance may be added from the secondary sampling port 11, for example, adding solvent. The addition of solvent increases the amount of liquid sample, and the sample solution is diluted or the solvent that can lower the viscosity of a liquid sample can be added.

Figure 20:
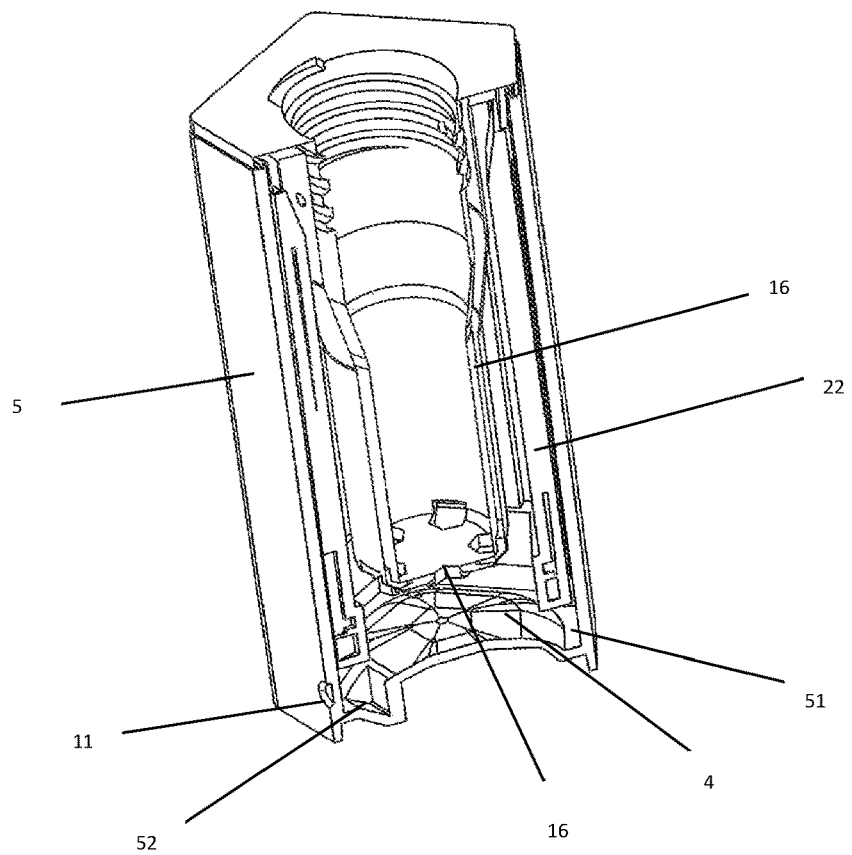
FIG. 20 is a cross-sectional view of the apparatus in an assembled state according to another embodiment of the present invention.

FIG. 20 shows a preferred mode of the detection apparatus of the present invention. In order to more clearly show the internal structure, the sample collector 2 is hidden in the figure. As shown in the figure, the sample receiving cup 1 is a regular pentahedron. The placement portion 22 for accommodating the detecting element is located in the space between the sleeve 16 and the cup body 5 sidewall, wherein the sample loading area or part of the sampling loading area of the detecting element is exposed from the slot opening of the placement portion, and is located in the first liquid collecting area 51 at the bottom of the cup body (the detecting element is not shown in the figure); the protrusion structure 4 at the bottom of the cup body is composed of five repeating units, and a third curved surface 43 of one of the units is provided with an outwardly chamber to constitute a second liquid collecting area 52. There is a secondary sampling port 11 on the cup body sidewall opposite to the opening 520 of the second liquid collecting area; there are five pentagonal notches 161 fixed at the bottom of the sleeve in the cup body, which are respectively located above the five second curved surfaces 42 of the protrusion structure at the bottom of the cup body, wherein the sleeve 16, the placement portion 22 are detachably connected to the cup body 5.

It is to be understood that the terms "first liquid collecting area, second liquid collecting area, first plane, first curved surface, second curved surface, . . . " in the present invention are merely used to facilitate the description of the structure of the detection apparatus rather than constitute any limitation to the present invention, for example, when referring to a first liquid collecting area, it does not necessarily mean that a second liquid collecting area is included.

The present invention further provides a method of using the apparatus for detecting an analyte in a liquid sample, which is described with reference to the embodiment of FIGS. 10~21. The collecting element 15 of the sample collector is placed in the mouth of a user, and the collecting element 15 continuously absorbs the saliva, then the collecting element 15 is taken out of the user's mouth and put into the sleeve 16 used with the collecting element 15. The fixing base 6 is rotated until the sleeve 16 opening is completely covered, the liquid sample cannot leak from the apparatus through the cover, and the positioning block 7 is screwed into the positioning groove to give a rotation indication. During the rotation, by squeezing the collecting element 15 that has absorbed liquid samples, the liquid samples on the collecting element 15 are squeezed from the notch 161 at the bottom of the sleeve, and liquid samples flow from the second curved surface 42 of the protrusion structure 4 at the bottom of the cup body to the third curved surface 43 and then enter the first liquid collecting area 51. The liquid samples on the first liquid collecting area 51 reach the detecting element 3 for detection thereon. At the same time, liquid samples in the first liquid collecting area 51 enter the second liquid sample collection area 52 through the opening 520. When a second confirmatory detection is required, the sampler is used to break the fragile element of the sealed secondary sampling port 11, to expose the secondary sampling port 11, and the sampler is extended to the second liquid collecting area 52 from the secondary sampling port 11 to draw liquid samples for second confirmatory detection.

In addition, the embodiments described in the following paragraphs are also a part of the present disclosure.

1. An apparatus for detecting analyte in a liquid sample, comprising a cup body, and the cup body includes a sidewall and a bottom, a first liquid collecting area is provided at the bottom of the cup body, wherein a second liquid collecting area is further provided at the bottom of the cup body.
2. The apparatus according to paragraph 1, wherein the cup body bottom further includes a protrusion structure protruding into the cup body, and the part of second liquid collecting area is disposed on the protrusion structure.
3. The apparatus according to paragraph 2, wherein the second liquid collecting area is a chamber.
4. The apparatus according to any one of paragraphs 1 to 3, wherein the second liquid collecting area is in fluidic communication with the first liquid collecting area.
5. The apparatus according to paragraph 1, wherein the apparatus further comprises a secondary sampling port, and the secondary sampling port is a puncturable structure.
6. The apparatus according to paragraph 5, wherein the secondary sampling port is disposed on a cup body sidewall opposite to the opening of the second liquid collecting area.
7. The apparatus according to paragraph 1, wherein the apparatus further comprises a detecting element, and the sampling loading area or part of the sampling loading area of the detecting element is located in the first liquid collecting area.
8. The apparatus according to paragraph 7, wherein the detecting element is disposed in a placement portion for placing a detecting element.
9. The apparatus according to paragraph 1, wherein the apparatus further comprises a sample collector, and the sample collector can be received and held in the cup body, and the collected samples are sent to the first liquid collecting area.
10. The apparatus according to paragraph 9, wherein the sample collector comprises a collecting element and a push rod.
11. The apparatus according to paragraph 10, wherein the collecting element is made of a sponge or a foam material.
12. The apparatus according to paragraph 1, wherein the apparatus further comprises a sleeve, the sleeve has an opening at one end and a closed surface at the other end, and a notch for allowing the liquid to flow out is disposed on the closed surface.

13. The apparatus according to paragraph 12, wherein the notch is located above the protrusion structure.

Furthermore, the present disclosure includes the embodiments described in the following paragraphs.

1. An apparatus for detecting analyte in a liquid sample, comprising a cup body, the cup body includes a sidewall and a bottom, the bottom of the cup body is convex toward the cup body to form a protrusion structure, and a first liquid collecting area is formed between the protrusion structure and the cup body sidewall, wherein the protrusion structure is used to guide liquid samples to enter the first liquid collecting area.
2. The apparatus according to paragraph 1, wherein the protrusion structure comprises a central top portion, and a slope extending from the central top portion to the first liquid collecting area along the periphery, and the liquid sample enters the first liquid collecting area via the surface of the slope.
3. The apparatus according to paragraph 2, wherein the slope is composed of a plurality of curved surfaces that are curved inwardly.
4. The apparatus according to paragraph 3, wherein the plurality of curved surfaces has different radians.
5. The apparatus according to paragraph 4, wherein the liquid sample enters the first liquid collecting area via one or more curved surfaces of the protrusion structure.
6. The apparatus according to paragraph 5, wherein the protrusion structure comprises a first curved surface, a second curved surface, and/or a third curved surface, wherein an end of the third curved surface is connected to the first liquid collecting area, and the liquid sample enters the first liquid collecting area through the second curved surface and the third curved surface.
7. The apparatus according to paragraph 6, the end of the third curved surface corresponds to the sample loading area of the detecting element.
8. The apparatus according to paragraph 6, wherein there is a smooth boss between the second curved surface and the third curved surface.
9. The apparatus according to any one of paragraphs 5 to 8, wherein both sides of the second curved surface and/or the third curved surface have structures restricting liquid flow.
10. The apparatus according to paragraph 9, wherein the structure for restricting liquid flow is a curved surface having a height higher than the second curved surface and/or the third curved surface.

Moreover, the present disclosure includes the embodiments described in the following paragraphs.

1. A placement portion for preventing flooding of a test strip, wherein the placement portion comprises a slot for accommodating a test strip, wherein the slot includes an anti-flooding structure, and the anti-flooding structure includes a recess disposed on the slot bottom plate.
2. The placement portion according to paragraph 1, wherein the slot forms a chamber for accommodating excess sample at the recess.
3. The placement portion according to paragraph 2, wherein there are one or more chambers.
4. The placement portion according to paragraph 3, wherein the chamber is rectangular.
5. The placement portion according to paragraph 2, wherein the card slot sidewall having a recess has a protrusion for clamping the test strip.
6. The placement portion according to paragraph 2, wherein the chamber is located in the sample loading area of the test strip, or upstream of the labeled area of the test strip, or between the sample loading area and the labeled area of the test strip.
7. The placement portion according to paragraph 1, wherein the anti-flooding structure divides the slot into two parts, i.e. a first portion having a recess on the slot bottom plate and a second portion having no recess on the slot bottom plate, wherein the width of the first portion is greater than that of the second portion.
8. The placement portion according to paragraph 7, wherein the second portion further includes a third portion having a width greater than the second portion.
9. The placement portion according to paragraph 8, wherein the third portion has a smaller width than the first portion.
10. The placement portion according to paragraph 9, wherein the third portion is located between the first portion and the second portion.
11. The placement portion according to paragraph 9, wherein the third portion is located in the sampling loading area of the test strip, or downstream of the sample loading area of the test strip, or between the sampling loading area and the labeled area of the test strip, or in the labeled area of the test strip.
12. The placement portion according to paragraph 8, wherein the width of the second portion is equal to or substantially equal to the width of the test strip.

The invention claimed is:

1. An apparatus for detecting analyte in a liquid sample, comprising:
   a cup body having a bottom and a sidewall;
   a protrusion structure provided at the bottom of the cup body as to make the bottom of the cup body in a concave shape;
   a first liquid collecting area that is formed between the protrusion structure and the cup body sidewall;
   wherein the protrusion structure comprises a central top portion, a first curved surface, a second curved surface, and a third curved surface, the first curved surface is connected to the central top portion, the second curved surface is connected to the first curved surface, the third curved surface is connected to the second curved surface, and an end of the third curved surface is connected to the first liquid collecting area;
   wherein the first curved surface, the second curved surface, and the third curved surface are curved inwardly, and the first curved surface, the second curved surface, and the third curved surface are configured to guide the liquid sample from the first curved surface, or the second curved surface, or the third curved surface or a combination thereof to the first liquid collecting area, and the second curved surface has a lower radian relative to the first curved surface and the third curved surface.

2. The apparatus for detecting analyte in a liquid sample according to claim 1, wherein the first liquid collecting area is a ring structure surrounding the protrusion structure.

3. The apparatus for detecting analyte in a liquid sample according to claim 1, wherein the first curved surface, the second curved surface or the third curved surface is an area for receiving the liquid sample, thereby forming an area similar to an equilateral triangle or an isosceles triangle on the protrusion structure.

4. The apparatus for detecting analyte in a liquid sample according to claim 1, wherein the apparatus further comprises a sample receiving cup that is fixed in the cup boy for receiving a collector element, and wherein the receiving cup include one or more notches.

5. The apparatus for detecting analyte in a liquid sample according to claim 4, wherein the one or more notches of the sample receiving cup is disposed above the first curved surface or the second curved surface or the third curved surface; or is disposed between the first curved surface and the second curved surface.

6. The apparatus for detecting analyte in a liquid sample according to claim 4, wherein the one or more notches is disposed above the second curved surface.

7. The apparatus for detecting analyte in a liquid sample according to claim 1, wherein the apparatus further comprises a second liquid collecting area and the second liquid collecting area includes a corner area for collecting samples for secondary sampling.

8. The apparatus for detecting analyte in a liquid sample according to claim 1, wherein a cross section of the cup body is in a pentagonal shape.

9. The apparatus for detecting analyte in a liquid sample according to claim 1, wherein a detecting element is provided in the first liquid collecting area.

10. The apparatus for detecting analyte in a liquid sample according to claim 1, wherein the apparatus further comprises a sample collector, the sample collector can be received and held in the cup body.

\* \* \* \* \*